United States Patent [19]

Kavadias

[11] 4,150,032
[45] Apr. 17, 1979

[54] 9-OXOBENZOMORPHAN PROCESS AND INTERMEDIATES

[75] Inventor: Gerry Kavadias, St. Lambert, Canada

[73] Assignee: Bristol-Myers Company, New York, N.Y.

[21] Appl. No.: 870,409

[22] Filed: Jan. 18, 1978

[51] Int. Cl.² ............... C07D 209/56; C07D 221/26
[52] U.S. Cl. .................. 260/325 R; 260/326.11 R; 260/340.9 R; 260/465 F; 260/574; 260/590 FA; 560/53; 546/97
[58] Field of Search ........................ 260/325 R

[56] References Cited

U.S. PATENT DOCUMENTS

| | | | |
|---|---|---|---|
| 3,853,889 | 12/1974 | Monkovic et al. | 260/293.55 |
| 3,891,657 | 6/1975 | Monkovic et al. | 260/293.54 |
| 3,959,290 | 5/1976 | Monkovic | 260/293.55 |

FOREIGN PATENT DOCUMENTS 7026133  3/1972  France.

OTHER PUBLICATIONS

Takeda et al., J. Org. Chem., vol. 37, pp. 2677–2679 (1972).
Murphy et al., J. Org. Chem., vol. 25, pp. 1386–1388 (1960).
Ahmed et al., Cam. J. Chem., vol. 53, pp. 3276–3284 (1975).
Evans et al., J. Org. Chem., vol. 35, pp. 4122–4127 (1970).

*Primary Examiner*—Alton D. Rollins
*Attorney, Agent, or Firm*—Robert H. Uloth

[57] ABSTRACT

Improved processes for preparing 2'-alkoxy-2,5-di-substituted-9-oxo-6,7-benzomorphans from benz[e]indolines and synthesis of the benz[e]indoline intermediates are described. A representative example involves synthesis of 9b-allyl-8-methoxy-3-methyl-5,9b-dihydrobenz[e]indoline and bromination thereof to 9b-allyl-4-bromo-8-methoxy-2,4,5,9b-tetrahydro-1H-benz[e]indole methylbromide which is then hydrolyzed with a weak base such as ammonium bicarbonate to provide 5-allyl-2'-methoxy-2-methyl-9-oxo-6,7-benzomorphan.

5 Claims, No Drawings

9-OXOBENZOMORPHAN PROCESS AND INTERMEDIATES

DESCRIPTION OF THE PRIOR ART (1) Takeda, et al., J. Org. Chem. 37 (17), 2677–2679 (1972) describes an improved synthesis of a 9-oxo-6,7-benzomorphan of formula (5) as outlined below (2) Monkovic, et al., U.S. Pat. No. 3,891,657 describes an improved process for the preparation of 2'-methoxy-2,5-dimethyl-9-oxo-6,7-benzomorphan (4) involving catalytic debenzylation of methobromide (3) which in turn is obtained by alkylating ketone (1) with 2-benzylmethylaminoethylchloride followed by bromination of the hydrobromide salt of (2) with subsequent neutralization of the brominated material with ammonium hydroxide.

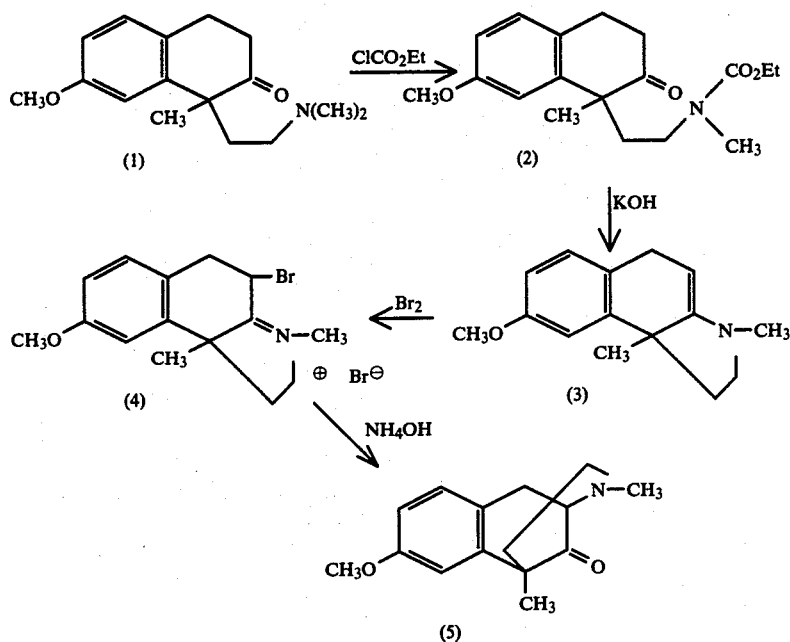

According to Takeda, et al., the dihydrobenz[e]indoline intermediate (3) was prepared from the naphthalenone (1) in 48% overall yield and converted to the 9-oxobenzomorphan (5) in 60% yield without isolation of the intermediate bromoiminium bromide (4). The 9-oxobenzomorphan (5) was obtained by treating the bromoiminium bromide (4) with aqueous ammonium hydroxide. According to Takeda, et al., the use of hydroxide is essential to the rearrangement of (4) to (5) since substitution of anhydrous triethylamine for aqueous ammonium hydroxide did not give (5).

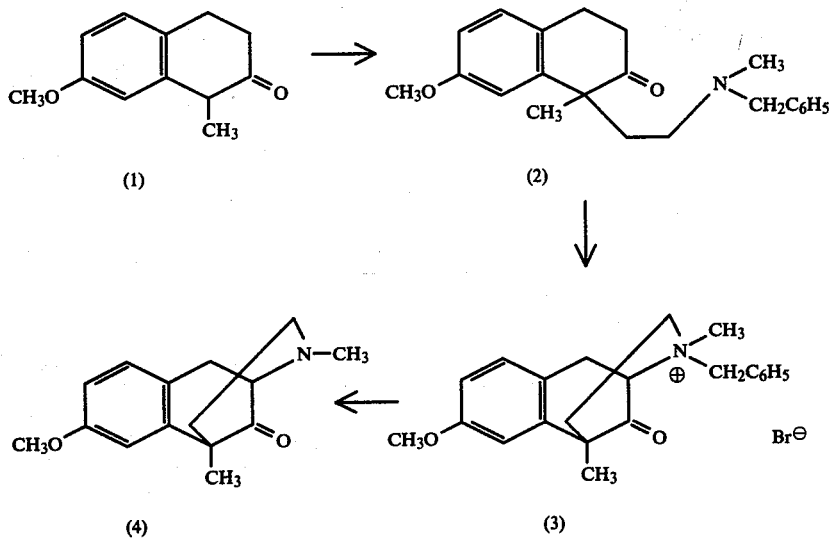

(3) Murphy, et al., J. Org. Chem. 25, 1386–1388 (1960) and Ahmed, et al., Can. J. Chem., 53, 3276–3284 (1975) describe the synthesis of 2'-methoxy-2,5-dimethyl-9-oxo-6,7-benzomorphan (5) by pyrolysis of the corresponding methobromide (4) according to the following flow-sheet. The methobromide intermediate (4) was obtained by a multi-step process involving dimethylaminoethylation of ketone (1) and bromination of the hydrobromide salt of the alkylated ketone (2) to provide the hydrobromide salt of bromo-ketone (3)

which neutralized with ammonia cyclized to the methobromide (4) intermediate.

according to the procedure described by Murphy, et al., J. Org. Chem., 25, 1386–1388 (1960).

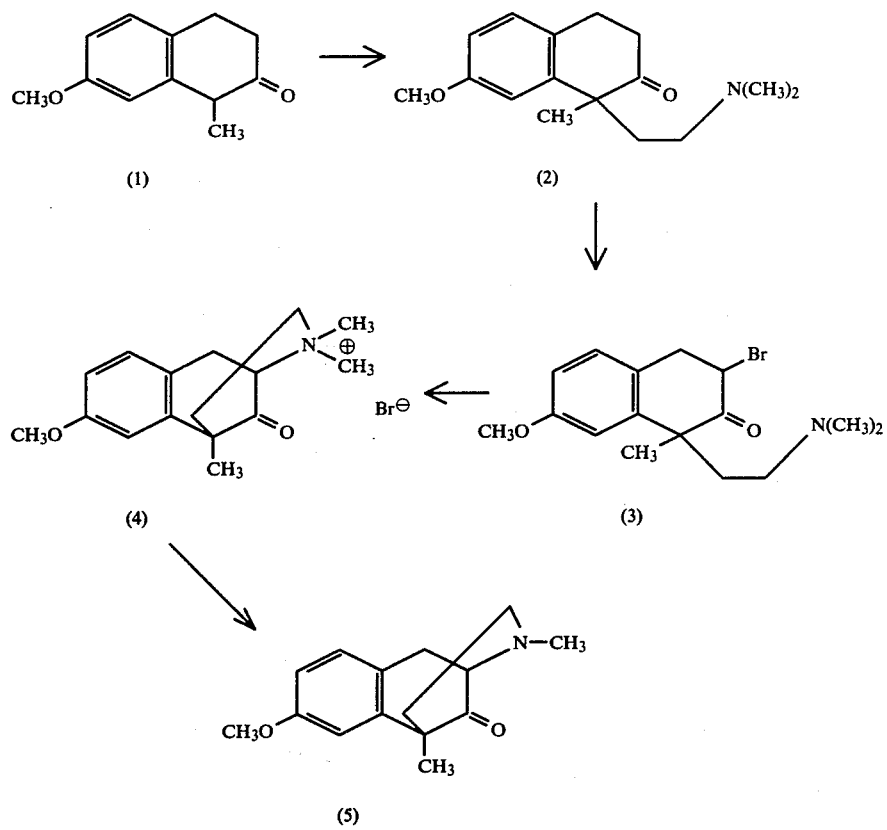

(4) Monkovic, et al., U.S. Pat. No. 3,853,889 and U.S. Pat. No. 3,959,290 and Ahmed, et al., Can. J. Chem., 53, 3276–3284 (1975) describe the synthesis of 2'-methoxy-2-methyl-5-allyl-9-oxo-6,7-bezomorphan (5) French Patent 2,096,914-Q (Derwent Abstracts No. 31347T-B) describes the synthesis of benzoindoles (4) from tetralone starting materials (1) according to the following scheme in which substituents R, $R^1$ and $R^2$ are alkyl and Y represents hydrogen, hydroxy, and alkoxy.

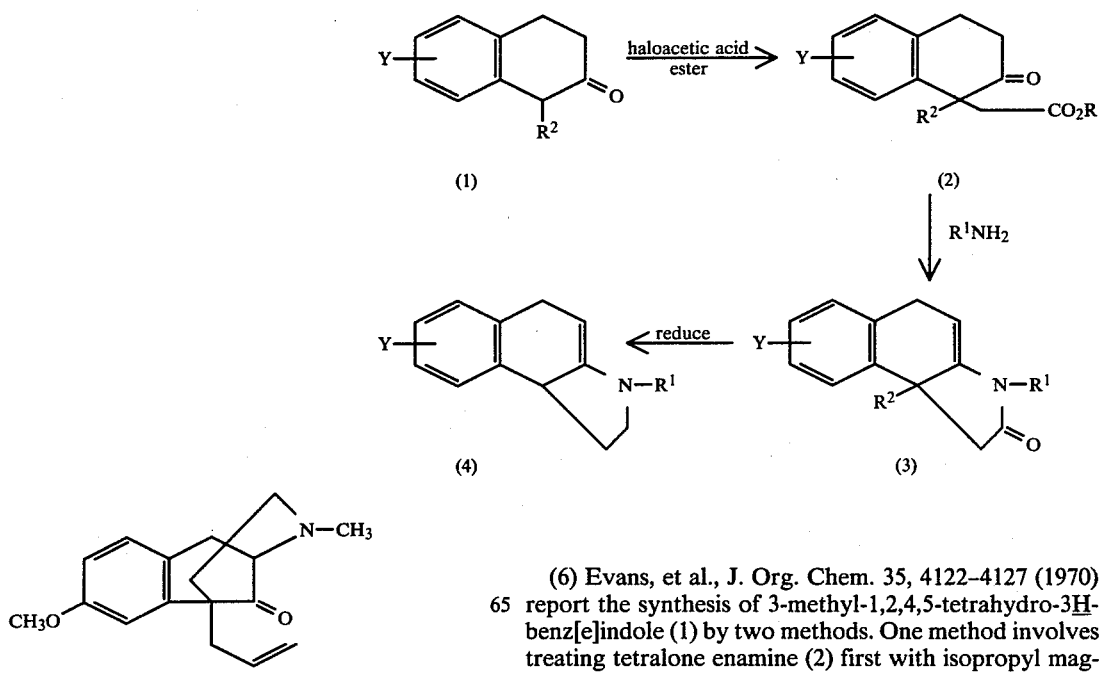

(6) Evans, et al., J. Org. Chem. 35, 4122–4127 (1970) report the synthesis of 3-methyl-1,2,4,5-tetrahydro-3H-benz[e]indole (1) by two methods. One method involves treating tetralone enamine (2) first with isopropyl magnesium chloride and then with bromochloroethane. The second method involves hydrolysis of the ketone amine (3).

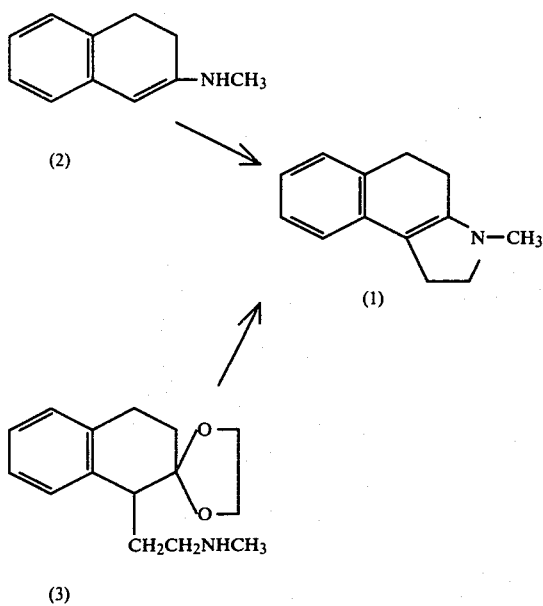

SUMMARY OF THE INVENTION

In its broadest aspect, this invention is concerned with a process for preparing 2'-alkoxy-2,5-di-substituted-9-oxo-6,7-benzomorphans having formula I (I)

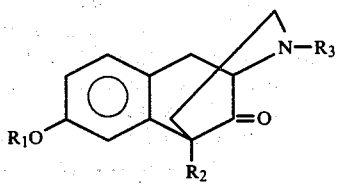

in which

R₁ is lower alkyl or benzyl;

R₂ is lower alkyl, allyl, benzyl, or

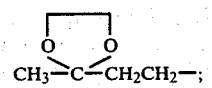

R₃ is lower alkyl,

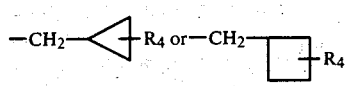

in which R₄ is hydrogen or methyl.

Such 9-oxo-6,7-benzomorphans are valuable intermediates employed in the preparation of analgesics, narcotic antagonists and antitussives described in Monkovic, et al., U.S. Pat. Nos. 3,891,657; 3,853,889; 3,959,290; 3,966,747; Montzka, et al., U.S. Pat. No. 3,956,336 and Albertson, U.S. Pat. No. 4,009,171.

The instant process involves conversion of a benz[e]indoline (e.g. 9b-allyl-8-methoxy-3-methyl-5,9b-dihydrobenz[e]indoline) to the corresponding 9-oxo-6,7-benzomorphan (e.g. 5-allyl-2'-methoxy-2-methyl-9-oxo-6,7-benzomorphan) by brominating the dihydrobenz[e]indoline to provide a bromoenaminium bromide intermediate which is then hydrolyzed and rearranged with weak bases (e.g. ammonium bicarbonate or sodium bicarbonate) or activated aluminum oxide. Additional aspects of the invention are concerned with processes for the preparation of the benz[e]indoline starting materials and novel intermediates therefor.

DETAILED DESCRIPTION OF THE INVENTION

The 2'-alkoxy-2,5-disubstituted-9-oxo-6,7-benzomorphan of the invention have the basic 6,7-benzomorphan nucleus illustrated by numbered planar formula I.

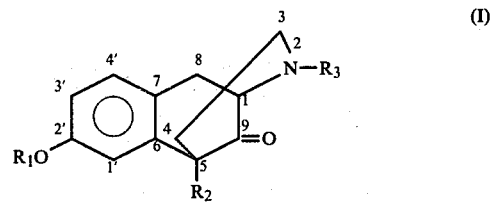

Numbered planar formula II depicts the basic nucleus of the benz[e]indolines employed in preparation of the "6,7-benzomorphans".

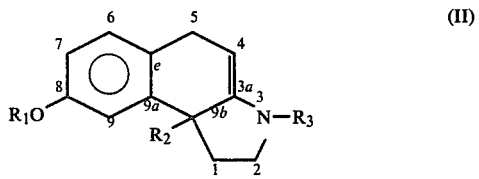

For the purpose of this disclosure the term "lower alkyl" refers to a carbon chain of 1 to 4 carbon atoms inclusive wherein the carbon chain is comprised of both straight and branched chain carbon radicals. Exemplary of these carbon chain radicals are methyl, ethyl, propyl, isopropyl, 1-butyl, 1-methylpropyl, 2-methylpropyl and tert.-butyl.

The following chart illustrates the process of the invention for converting benz[e]indolines of formula II to the formula I 9-oxo-6,7-benzomorphans wherein R₁, R₂ and R₃ are as defined above.

CHART I

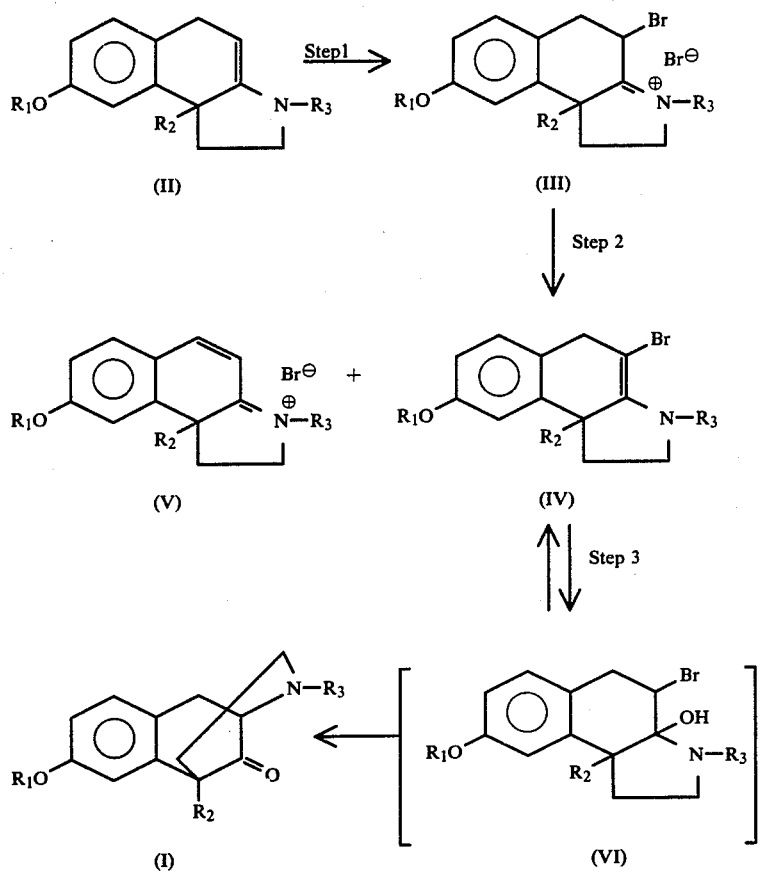

Examples of 9-oxo-6,7-benzomorphan provided by the above process are those compounds of formula I wherein $R_1$, $R_2$ and $R_3$ are as defined in Table 1 below.

| | Formula I Compounds | | |
|---|---|---|---|
| | $R_1$ | $R_2$ | $R_3$ |
| (Ia) | methyl | allyl | methyl |
| (Ib) | methyl | methyl | methyl |
| (Ic) | benzyl | allyl | methyl |
| (Id) | methyl | $CH_3-C(-O-CH_2CH_2-)(-O-)$ | methyl |
| (Ie) | methyl | allyl | $-CH_2-\triangleleft$ (cyclopropyl) |
| (If) | methyl | allyl | $-CH_2-\square$ (cyclobutyl) |
| (Ig) | benzyl | allyl | $-CH_2-\square$ (cyclobutyl) |
| (Ih) | methyl | benzyl | methyl |
| (Ii) | methyl | methyl | $-CH_2-\triangleleft^{CH_3}$ |

In carrying out step 1 of the process outlined in Chart I, benz[e]indolines of Formula II are brominated to provided bromoenaminium bromides of Formula III. The bromination is preferably carried out by adding a solution of the benz[e]indoline II in methylene chloride to a solution of bromine in the same solvent while maintaining a reaction temperature in the range of $-40°$ to $-70°$. The addition of the methylene chloride solution of the benz[e]indoline II is carried out rapidly by all-at-once mixing in a batchwise fashion. The reverse process wherein a methylene chloride solution of bromine is added batch-wise to a solution of the formula II benz[e]indoline is also satisfactory and provides similar yields of III. However, if a methylene chloride solution of bromine is added drop-wise to a solution o benz[e]indoline II in methylene chloride, the bromoenaminium bromide III is contaminated with appreciable quantities of the hydrobromide salt of the starting enamine II and the yield is substantially lower. Selection of the reaction solvent is also critical in step 1 as well as the mode of addition of the reactants. For instance, when a solution of bromine in ether is added gradually to a solution of IIa ($R_1=R_3=$methyl, $R_2=$allyl) in methylene chloride at $-60°$, the material obtained is mainly the hydrobromide of IIa. Suitable solvents for carrying out step 1 are halogenated hydrocarbons (e.g., methylene chloride, chloroform and ethylene chloride).

The formula III bromoenaminium bromides are converted to the formula I 9-oxo-benzomorphans by treatment with a weak base such as sodium or ammonium bicarbonate in aqueous ethanol or, alternatively, by treatment with activated aluminum oxide in aqueous dimethylsulfoxide. The reaction is believed to proceed by fast formation of the bromoenamines of formula IV (step 2) which slowly hydrate to carbinol amines of formula VI (step 3) with subsequent rearrangement to products of formula I. In carrying out the hydrolysis of the compounds of formula III, the type and quality of base, the mode of addition of the base, the solvent effect and the temperature and the duration of the reaction all affect yields of the formula I products.

Preferred reaction conditions for hydrolyzing bromoenaminium bromides (III) to 9-oxo-6,7-benzomorphans I comprise adding an aqueous solution of one molecular equivalent of ammonium bicarbonate dropwise in a period of one to two hours to a solution of III in 95% ethanol while maintaining a temperature of −5° to −15°, followed by stirring of the reaction mixture at −5° to −15° for a period of 1.0 to 3.0 hours, and then at room temperature for a period of 20–28 hr. The 9-oxo-benzomorphans of formula I are obtained in this manner in yields ranging from 35 to 65%. Substantially lower yields are, however, obtained if the bicarbonate solution is added all-at-once to the formula III compound. When stronger bases such as sodium hydroxide, potassium hydroxide or ammonium hydroxide are employed, the yields of I are almost nil. There is only one exception in this application. When compound IIIb ($R_1=R_2=R_3CH_3$) is treated with a strong base (ammonium hydroxide) compound Ib is obtained in 21% yield. For instance, when an aqueous ethanol solution of IIIa ($R_1=R_3=$methyl, $R_2=$allyl) is treated with one or two equivalents of sodium hydroxide or ammonium hydroxide, the product isolated contained only a trace of the desired 9-oxo-benzomorphan of formula I.

In the initial stage of step 2, the bromoenaminium compound of formula IV precipitates as a solid or oil and the slowly dissolves as the reaction progresses. The formula IV intermediates may be isolated, if desired, and then treated with aqueous ethanol to provide formula I products.

As shown in Chart I, base treatment of formula III compounds (step 2) proceeds in two directions providing bromoenamines of formula IV which are precursor of the products of formula I along with substances of formula V which are not precursors of formula I compounds. The ratio of IV and V is dependent upon the base employed. With strong bases such as sodium hydroxide, potassium hydroxide, and ammonium hydroxide the major product is the unwanted contaminant V.

The benz[e]indoline intermediates of formula II are synthesized according to processes outlined in Charts II, III and IV.

CHART II<sup>a</sup>

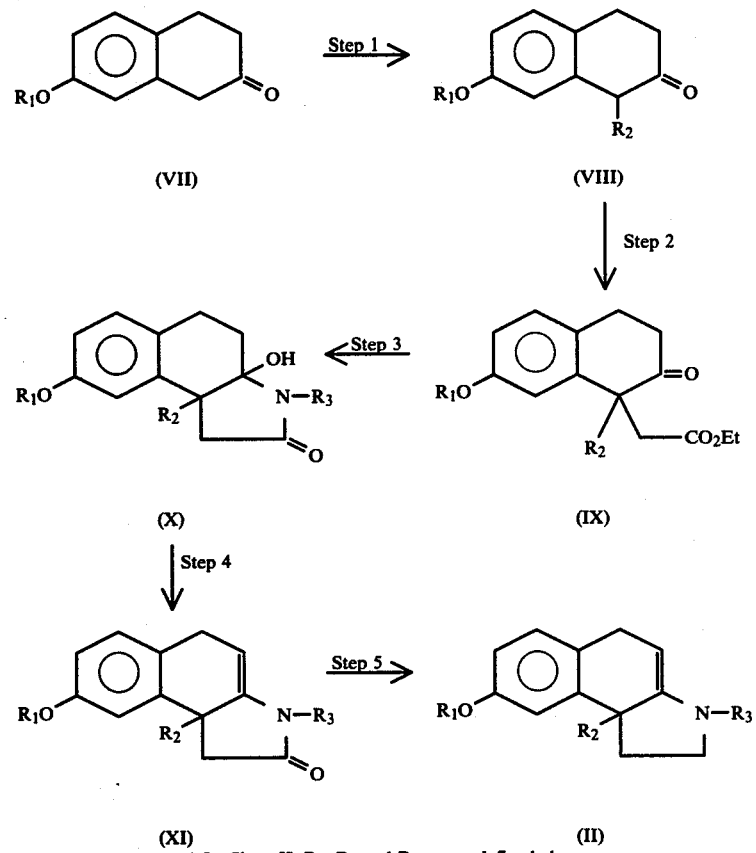

a) In Chart II, $R_1$, $R_2$ and $R_3$ are as defined above.

Step 1 of the process outlined in Chart II is carried out by alkylation of 7-(benzyloxy or alkoxy)substituted-2-tetralones VII according to the procedure described by Murphy, et al., J. Org. Chem. 25, 1386 (1960) to provide 1-mono-substituted compounds of formula VIII in 60–95% yields. In step 2, the sodium enolates of VIII are alkylated with ethyl bromoacetate in dimethylformamide to provide 1,1-disubstituted derivatives of formula IX. Reaction of formula IX compounds with excess amine of the formula $R_3$—$NH_2$ wherein $R_3$ is as defined above in an alkanol solvent such as ethanol at room temperature provides hydroxy lactams X in 80–90% yields (step 3). The formula X hydroxy lactams are relatively stable in crystalline form and in solution at temperatures below 40°. At higher temperatures, water is eliminated and hydroxy lactams X are quantitatively converted to unsaturated lactams of formula XI (step 4). The conversion to XI is preferably carried out by refluxing a solution of X in reaction inert solvents such as benzene or toluene with a catalytic amount of an acid such as p-toluenesulfonic acid. Reduction of the unsaturated lactams XI with lactium aluminum hydride in a reaction inert solvent such as ether provides corresponding enamines of formula II in yields of 90-98%. Overall yields of this 5-step reaction based on the tetralone starting materials of formula VII range from about 25 to 65%. Representative examples of benz[e]indolines of formula II and overall yields of the 5-step process based on the tetralones starting materials of formula VII are given in Table II below.

TABLE II

Yields of Formula II Compounds From Tetralones VII

| Compound | $R_1$ | $R_2$ | $R_3$ | Yield |
|---|---|---|---|---|
| (IIa) | methyl | allyl | methyl | 62% |
| (IIb) | methyl | methyl | methyl | 58% |
| (IIc) | benzyl | allyl | methyl | 51% |
| (IId) | methyl | $-CH_2CH_3\overset{O\phantom{xx}O}{\underset{}{-C-}}CH_3$ | methyl | 27% |

The benz[e]indolines of formula II are light-brown colored oily substances very sensitive to air and are preferably used in the preparation of the compounds of formula I immediately after preparation with all operational manipulation required for synthesis, such as filtration, evaporation and release of vacuum, performed under a nitrogen atmosphere. When storage of the benz[e]indolines of formula II is required, they are converted to a picrate salt which can be stored at room temperature for several months and then quantitatively converted to the benz[e]indoline bases by alkaline treatment.

mula VII. In step 1, conversion of formula VII to enamines of formula XII is carried out according to conventional procedures described by D. A. Evans, et al., J. Org. Chem. 35, 4122 (1970). Treating enamines of formula XII with isopropyl magnesium chloride provides "bidentate" nucleophiles which are then alkylated by reaction with bromochlorethane (refer to Evans, et al. supra) to produce benz[e]indolines of formula XIII in 95 to 99% yield (step 2). In step 3, the benz[e]indolines of formula XIII are alkylated at the "9b" position with $R_3X$ halides wherein $R_3$ is as defined above and X is halogen (preferably chlorine or bromine). To some extent N-alkylation is a competing reaction and the ratio of the desired C-alkylated products to unwanted N-alkylated compounds varies with the alkylating agent and the solvent. Thus, alkylation of XIII with allyl bromide in acetonitrile proceeds mainly by C-alkylation to produce the corresponding 9b-allyl hydrobromides XIV in 65-75% yields as pure crystalline salts. The effect of the solvent is more pronounced when benzyl chloride was employed as the alkylating agent. For instance, reaction of XIIIe ($R_1 = R_3 =$ methyl) with benzyl chloride in a reaction inert solvent such as benzene or dioxane or preferably acetonitrile produced XIVe ($R_1 = R_3 =$ methyl) as the picrate salt in yields of 10, 39, and 46%, respectively. Alkylation of XIIIe with methyl iodide in benzene or acetonitrile provides the "methiodide" of XIIIe as the major product. Formula XIV intermediates are purified either by crystallization as hydro-halide salts or by conversion to crystalline picrate salts. Such salts are stable and can be conveniently stored at room temperature for several months and when treated with base are quantitatively converted to the benz[e]indolines of formula II.

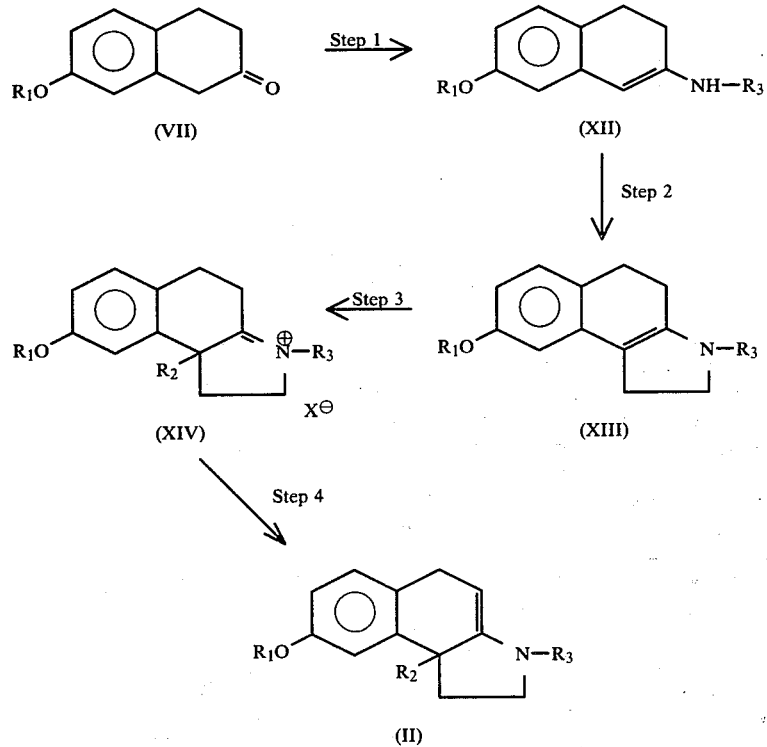

a) In Chart III, R, $R_2$ and $R_3$ are as defined above.

Chart III illustrates the synthesis of benz[e]indolines of formula II from 2-tetralone starting materials of for-

CHART IV[a]

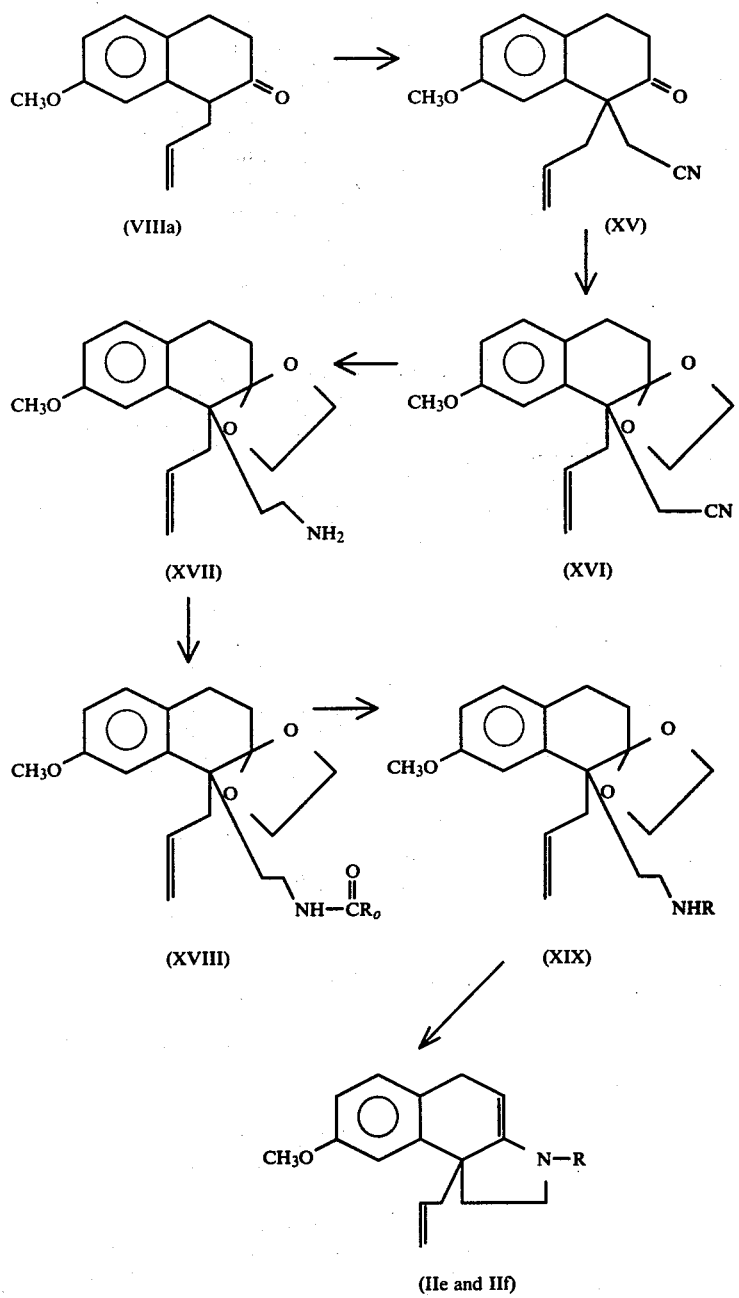

(IIe and IIf)

[a] In Chart IV, $R_o$ is cyclopropyl or cyclobutyl and R is cyclopropylmethyl or cyclobutylmethyl.

The reaction scheme of Chart IV illustrates an alternate preparation of 9b-allyl-3-cyclopropylmethyl-8-methoxy-1,2,4,5-tetrahydro-3H-benz[e]indole (IIe) and 9b-allyl-3-cyclobutylmethyl-8-methoxy-5,9b-dihydrobenz[e]indoline (IIf).

As indicated hereinabove, one aspect of the instant invention is concerned with a process for preparing 2'-alkoxy-2,5-di-substituted-9-oxo-6,7-benzomorphan compounds of formula I

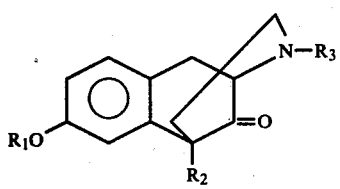

wherein
$R_1$ is lower alkyl or benzyl;
$R_2$ is lower alkyl, allyl, benzyl, or

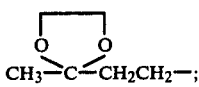

R₃ is lower alkyl,

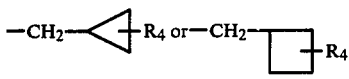

in which R₄ is hydrogen or methyl;
which comprises sequential steps of,
(a) brominating a dihydrobenz[e]indoline of formula II

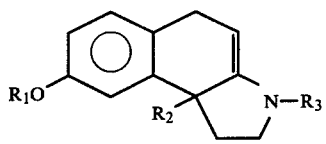

in which R₁, R₂, and R₃ are as recited above to produce a bromoenaminium bromide compound having formula III

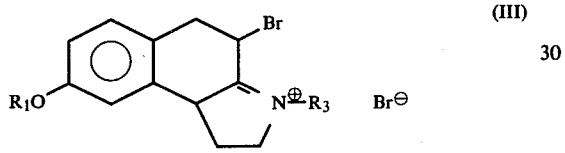

in which R₁, R₂, and R₃ are as recited above;
(b) treating the formula III compound with a bicarbonate base or activated aluminum oxide to produce the 9-oxo-6,7-benzomorphan compound of formula I.

Preferred embodiments of the foregoing process for the preparation of the 6,7-benzomorphan compounds characterized by formula I are those wherein:

(1) the formula II compound employed is that wherein R₁ and R₃ are methyl and R₂ is allyl;
(2) the formula II compound employed is that wherein R₁, R₂ and R₃ are methyl;
(3) the formula II compound employed is that wherein R₁ is benzyl, R₂ is allyl, and R₃ is methyl;
(4) the formula II compound employed is that wherein R₁ and R₃ are methyl and R₂ is (3-ethylenedioxy)butyl;
(5) the formula II compound employed is that wherein R₁ is methyl, R₂ is allyl and R₃ is cyclopropylmethyl;
(6) the formula II compound employed is that wherein R₁ is methyl, R₂ is allyl and R₃ is cyclobutylmethyl;
(7) the formula II compound employed is that wherein R₁ is benzyl, R₂ is allyl and R₃ is cyclobutylmethyl;
(8) the formula II compound employed is that wherein R₁ and R₃ are methyl and R₂ is benzyl;
(9) In step (a), the bromination is carried out by combining batchwise a methylene chloride solution of the formula II benz[e]indoline and a solution of bromine in methylene chloride at a temperature in the range of −40° to −70°;
(10) In step (a), the bromination reaction is carried out at a temperature of −40° to −70° for a period of 5-15 minutes and then at room temperature for 15-30 minutes;
(11) In step (a), the bromination reaction is carried out at a temperature of −60° for a period of 5-15 minutes and completed at room temperature in 15-30 minutes;
(12) In step (b), the bicarbonate base is selected from the group consisting of potassium bicarbonate, sodium bicarbonate and ammonium bicarbonate;
(13) In step (b), an ethanolic solution of the formula III compound and an aqueous solution of one molecular equivalent of a bicarbonate base selected from the group consisting of sodium bicarbonate, potassium bicarbonate, and ammonium bicarbonate are combined dropwise in a period of 1-2 hours at a temperature of −5° to −15°, followed by stirring the reaction mixture at −5° to −15° for a period of 1-3 hours and then at room temperature for a period of 20-28 hours.
(14) In step (b), the formula III compound is treated with activated aluminum oxide in aqueous dimethylsulfoxide.

A preferred embodiment in the process for preparing 2'-alkoxy-2,5-di-substituted-9-oxo-6,7-benzomorphan compounds of formula I

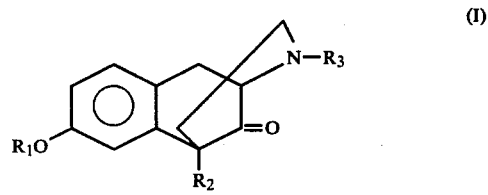

wherein
R₁ is lower alkyl or benzyl;
R₂ is lower alkyl, allyl, benzyl, or

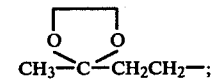

R₃ is lower alkyl,

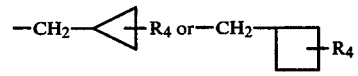

in which R₄ is hydrogen or methyl;
which comprises sequential steps of,
(a) combining rapidly batchwise a methylene chloride solution of a dihydro[e]indoline of formula II

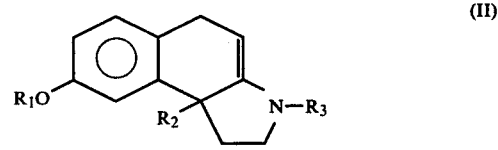

wherein the symbols "R₁, R₂ and R₃" are as recited above with an equimolar amount of bromine in methylene chloride at a temperature of about −60° under a nitrogen atmosphere, followed by stirring for about 10-15 minutes at −60° and finally at room temperature for about 20-30 minutes;
(b) treating the formula III compound in ethanol with an aqueous solution of a bicarbonate base selected from the group consisting of sodium bicarbonate, potassium bicarbonate and ammonium bicarbonate.

A preferred embodiment in the process for preparing 2'-alkoxy-2,5-di-substituted-9-oxo-6,7-benzomorphan compounds of formula I

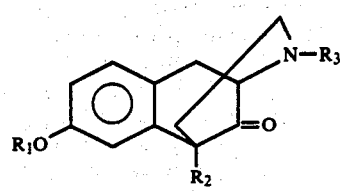

(I)

wherein
$R_1$ is lower alkyl or benzyl;
$R_2$ is lower alkyl, allyl, benzyl, or

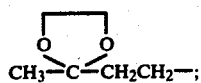

$R_3$ is lower alkyl,

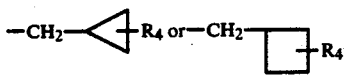

in which $R_4$ is hydrogen or methyl;
which comprises sequential steps of,
(a) combining rapidly a methylene chloride solution of a dihydro[e]indoline of formula II

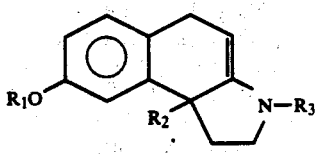

(II)

wherein the symbols "$R_1$, $R_2$ and $R_3$" are as recited above with an equimolar amount of bromine in methylene chloride at a temperature of about $-60°$ under a nitrogen atmosphere, followed by stirring for about 10–15 minutes at $-60°$ and finally at room temperature for about 20–30 minutes;
(b) treating the formula III compound with activated aluminum oxide.

Another aspect of the invention is directed to a process for preparing benz[e]indolines having formula II

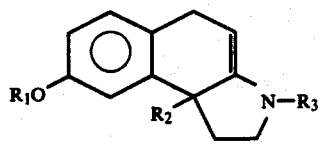

(II)

wherein
$R_1$ is lower alkyl or benzyl;
$R_2$ is lower alkyl, allyl, benzyl, or

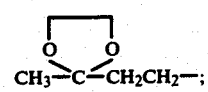

$R_3$ is lower alkyl,

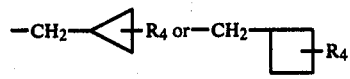

in which $R_4$ is hydrogen or methyl;
which comprises sequential steps of:
(a) reacting a compound of formula IX

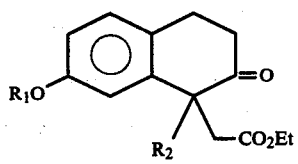

(IX)

wherein $R_1$ and $R_2$ are as recited above with an amine of the formula $R_3$—$NH_2$ wherein $R_3$ is as recited above to produce a hydroxy lactam compound having formula X

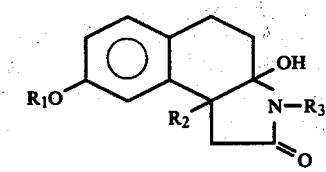

(X)

in which $R_1$, $R_2$, and $R_3$ are as recited above;
(b) heating the formula X compound above 40° to produce an unsaturated lactam having formula XI

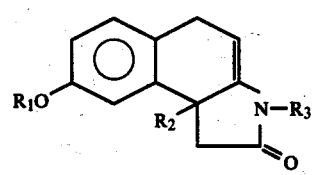

(XI)

in which $R_1$, $R_2$ and $R_3$ are as recited above;
(c) reducing the carbonyl function of compound XI by treatment with lithium aluminum hydride in a reaction inert solvent to provide the compound of formula II.

Preferred embodiments of the foregoing process for the preparation of the benz[e]indoline compounds characterized by formula II are those wherein:
(1) In step (a), a solution of X in benzene is refluxed;
(2) In step (b), a solution of X in benzene is refluxed with a trace of p-toluenesulfonic acid.

A further aspect of the invention is directed to a process for preparing benz[e]indolines having formula II

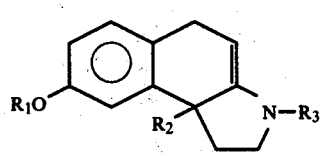

(II)

wherein
$R_1$ is lower alkyl or benzyl;
$R_2$ is lower alkyl, allyl, benzyl, or

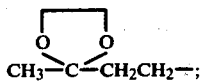

R₃ is lower alkyl,

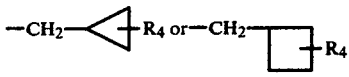

in which R₄ is hydrogen or methyl;
which comprises sequential steps of:
(a) alkylating a compound of formula XIII

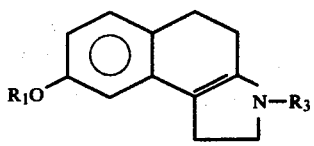
(XIII)

in which R₁ and R₃ are as recited above with R₂X wherein R₂ is as defined above and X is halogen in a reaction inert solvent to produce a compound having formula XIV

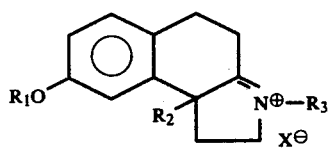
(XIV)

in which R₁, R₂ and R₃ are as recited above;
(b) neutralizing the formula XIV compound to provide the compound of formula II.

Another embodiment of the instant invention concerns a process for preparing benz[e]indolines having formula IIe and IIf

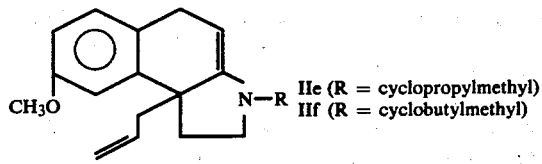

IIe (R = cyclopropylmethyl)
IIf (R = cyclobutylmethyl)

wherein
R is cyclopropylmethyl or cyclobutylmethyl which comprises hydrolyzing a compound of formula XIX

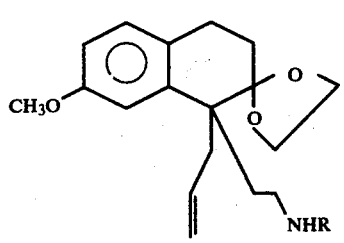
(XIX)

wherein

R is cyclopropylmethyl or cyclobutylmethyl with dilute solution of a strong acid such as hydrochloric acid, sulfuric acid or phosphoric acid.

As used herein, the term "reaction inert solvent" refers to a solvent that does not enter into a reaction to the extent that it emerges unchanged from the reaction.

The following examples further illustrate the present invention and will enable others skilled in the art to understand it more completely. It is to be understood that the invention is not limited solely to the particular examples given below. All temperatures expressed herein are in degrees centigrade. IR means infrared spectrum. The nuclear magnetic resonsance (NMR) spectra were recorded on a Varian A-60A spectrometer using deuteriochloroform as a solvent. The chemical shifts are expressed in δ values using tetramethylsilane as internal reference.

EXAMPLE 1

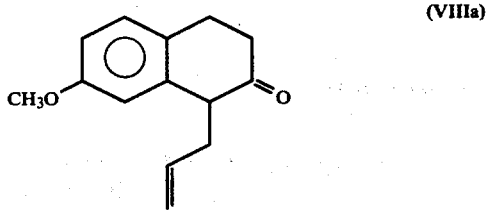
(VIIIa)

1-Allyl-3,4-dihydro-7-methoxy-2(1H)naphthalenone

To a solution of 104.1 g (0.59 mole) 3,4-dihydro-7-methoxy-2(1H)naphthalenone in 100 ml dry benzene was added dropwise under nitrogen with stirring at room temperature 62.5 g (0.88 mole) pyrrolidine. After the addition (10–15 min), the reaction mixture was refluxed for 2.5 hr with azeotropic removal of water and then cooled to room temperature. The enamine solution was added dropwise to 143.8 g (1.19 mole) allyl bromide with stirring at a rate sufficient to maintain normal refluxing to provide a heavy precipitate. Benzene (50 ml) was added to facilitate stirring and reflux continued for 4 hr; then, 700 ml of water was added and refluxing resumed. After 2 hr, the reaction mixture was cooled to room temperature and diluted with 100 ml benzene. The benzene layer was separated and the aqueous phase extracted with benzene (2×100 ml). The combined extracts were washed with water (2×100 ml) and dried (Na₂SO₄). After evaporation of the solvent, the residue was distilled to give 113.5 g (89%) of VIIIa, b.p. 114°–118°/0.1–0.05 mm Hg. NMR: δ 2.40–3.10 (m, 6, allylic and alicyclic), 3.45 (t, 1, C₁—H, J=6.5), 3.75 (s, 3, OCH₃), 4.8–6.1 (m, 3, olefinic), 6.7–7.2 (m, 3, ArH). IR: (neat) 1715 cm⁻¹.

EXAMPLE 2

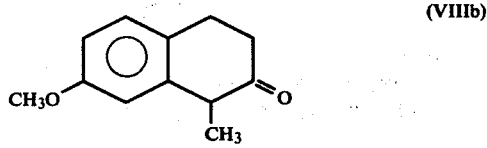
(VIIIb)

3,4-Dihydro-7-methoxy-1-methyl-2(1H)naphthalenone

This compound was prepared in 84% yield according to the method described by Murphy, et al., J. Org. Chem. 25, 1386 (1960); b.p. 110°–112°/0.3—0.4 mm Hg;

NMR: δ 1.43 (d, 3, CH₃, J=7.0 Hz), 3.68 (s, 3, OCH₃), 6.65–7.20 (m, 3, ArH).

EXAMPLE 3

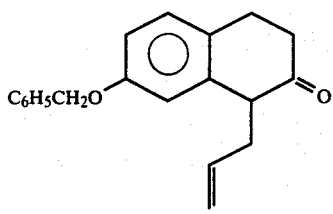

1-Allyl-7-benzyloxy-3,4-dihydro-2(1H)-naphthalenone

To a mixture of 22.7 g (0.09 mole) 3,4-dihydro-7-benzyloxy-2-(1H)naphthalenone and 50 ml dry benzene was added dropwise at room temperature a solution of 9.6 g (0.135 mole) pyrrolidine in 50 ml benzene with stirring under a nitrogen atmosphere. After the addition (10 min), the reaction mixture was refluxed with azeotropic removal of water for 3 hr and then cooled to room temperature. A solution of 22.0 g (0.181 mole) allyl bromide in 25 ml benzene was added dropwise (10 min) to the reaction mixture which was then heated to reflux to provide a heavy precipitate. Benzene (100 ml) was added to facilitate stirring and refluxing continued for 4 hr. Water (200 ml) was added and reflux continued for another 2 hr. After the reaction mixture cooled to room temperature, the benzene phase was separated and the aqueous phase was extracted first with benzene (50 ml) and then with ether (100 ml). The combined extracts were washed with water (100 ml), dried (Na₂SO₄) and evaporated to dryness to give 24.8 g (94%) of liquid VIIIc. NMR: δ5.15 (s, 2, PhCH₂O), 4.8–6.1 (m, 5, olefinic plus PhCH₂O), 6.80–7.50 (m, 8, ArH). IR: (CHCl₃), 1715 cm⁻¹.

Anal. Calcd. for C₂₀H₂₀O₂: C, 82.14; H, 6.89. Found: C, 80.72; H, 6.75.

The material was used without further purification in Example 7.

EXAMPLE 4

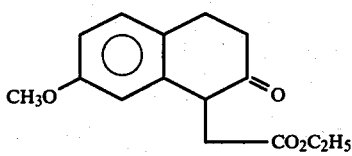

Ethyl-7-methoxy-2-oxo-1,2,3,4-tetrahydro-1-naphthalene-acetate

This compound was prepared in 78% yield according to Wiesner, et al., Can. J. Chem., 49, 1092 (1971).

EXAMPLE 5

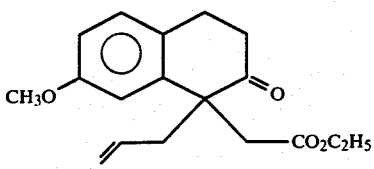

Ethyl-1-allyl-7-methoxy-2-oxo-1,2,3,4-tetrahydro-1-naphthaleneacetate

Into a flame-dry 500 ml 3-neck flask provided with mechanical stirrer, dropping funnel and a nitrogen inlet tube was placed 4.21 g sodium hydride (55% dispersion in oil, 100 mmol) with the apparatus placed under nitrogen. The oil was washed out with benzene (3×30 ml), 40 ml dry dimethylformamide was added and the suspension was stirred and cooled in an ice-bath. A solution of 21.6 g (100 mmol) 1-allyl-3,4-dihydro-7-methoxy-2(1H)naphthalenone (VIIIa) in 10 ml dimethylformamide was added dropwise (10 min), then the cooling bath was removed and stirring at room temperature continued until the evolution of gas ceased (2 hr). The brown-colored reaction mixture was cooled (ice-bath) and a solution of 16.7 g (100 mmol) ethyl bromoacetate in 40 ml dimethylformamide was added dropwise keeping the reaction temperature below 25° C. After the addition (15–20 min) stirring in cold was continued for 1 hr and then overnight at room temperature. Water (300 ml) was added and extracted with ether (3×100 ml). The combined ether extracts were washed with water (2×100 ml) dried (MgSO₄), the solvent removed by evaporation and the residue was distilled to give 26.0 g (86%) IXa, b.p. 145°–150°/0.05–0.01 mm Hg; IR (neat) 1740, 1715 cm⁻¹; NMR δ, 1.05 and 3.92 (triplet and quartet for OCH₂CH₃), 3.75 (s, 3, OCH₃), 4.65–6.0 (m, 3, CH=CH₂), 6.55–7.15 (m, 3, ArH).

Anal. Calcd for C₁₈H₂₂O₄: C, 71.50; H, 7.33. Found: C, 71.27; H, 7.28.

EXAMPLE 6

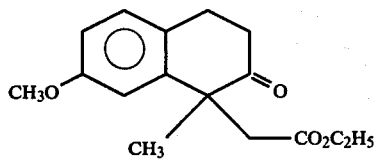

Ethyl 7-methoxy-1-methyl-2-oxo-1,2,3,4-tetrahydro-1-naphthaleneacetate

The compound 3,4-dihydro-7-methoxy-1-methyl-2(1H)-naphthalenone (VIIIb) (28.23 g, 148 mmol) was reacted with ethyl bromoacetate by the method of Example 5 to yield 36.0 g (88%) (IXb) b.p. 138°–140°/0.1 mm Hg; IR (neat) 1740 cm⁻¹ (unresolved ketone and ester bands); NMR δ, 1.05 and 3.93 (triplet and quartet for CO₂CH₂CH₃), 1.37 (s, 3, CH₃), 3.80 (s, 3, OCH₃), 6.6–7.3 (m, 3, ArH). The distillate crystallized on standing. A sample recrystallized from ethanol melted at 55°–55.5°.

Anal. Calcd. for C₁₆H₂₀O₄: C, 69.54; H, 7.29. Found: C, 69.75; H, 7.33. The distilled product was used in Example 10.

EXAMPLE 7

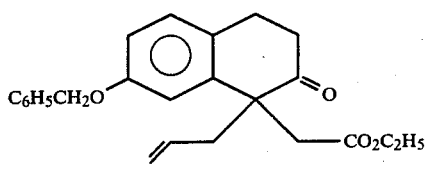
(IXc)

Ethyl-1-allyl-7-benzyloxy-2-oxo-1,2,3,4-tetrahydro-1-naphthaleneacetate

Crude 1-allyl-7-benzyloxy-3,4-dihydro-2(1H)-naphthalenone (VIIIc), 22.9 g (78.5 mmol) was reacted with ethyl bromoacetate by the method of Example 5 to yield 25.5 g (87%) crude crystalline IXc. Recrystallization from ethanol gave 19.5 g (66%) m.p. 83°–85°. IR (CHCl$_3$) 1725, 1710 cm$^{-1}$ (ketone and ester); NMR δ, 1.05 and 3.96 (triplet and quartet and OCH$_2$CH$_3$) 4.8–5.8 (m, 5, olefinic and PhCH$_2$O), 5.15 (s, 2, PhCH$_2$O), 6.80–7.55 (m, 8, ArH).

Anal. Calcd. for C$_{24}$H$_{26}$O$_4$: C, 76.16; H, 6.92. Found: C, 76.09; H, 6.96.

EXAMPLE 8

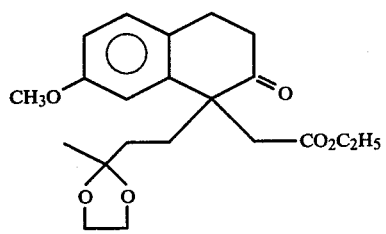
(IXd)

Ethyl-1-(3-ethylenedioxy)butyl-7-methoxy-2-oxo-1,2,3,4-tetrahydro-1-naphthaleneacetate This compound was prepared in 87% yield from ethyl-7-methoxy-2-oxo-1,2,3,4-tetrahydro-1-naphthaleneacetate (VIIId) according to Wiesner, et al., Can. J. Chem. 49, 1092 (1971) and used without purification in Example 12.

EXAMPLE 9

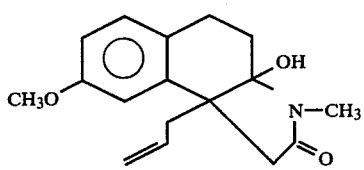
(Xa)

9b-Allyl-3a-hydroxy-8-methoxy-3-methyl-2-oxo-2,3,3a,4,5,9b-hexahydro-1H-benz[e]indole Methylamine (gas) 6.80 g (220 mmol) was added to ethanol in an open flask. This solution was added to 21.2 g (70 mmol) ethyl-1-allyl-7-methoxy-1,2,3,4-tetrahydro-1-naphthaleneacetate (IXa) and the clear solution left at room temperature for 24 hr to provide a crystalline product which was filtered to give 12.5 g (62%) Xa, m.p. 146°–149°. From the mother liquor, after evaporation (35°) and treatment of the residue with ether (50 ml), 3.8 g, m.p. 147°–150° additional Xa was obtained, increasing the yield to 81.5%; IR (CHCl$_3$) 3500 (broad band), 1690, 1615, 1505, cm$^{-1}$; NMR 2.88 (s, 3, N—CH$_3$), 3.92 (s, 3, OCH$_3$), 4.62 (broad singlet, OH), 4.9–6.1 (m, 3, olefinic), 6.8–7.3 (m, 3, ArH).

Anal. Calcd. for C$_{17}$H$_{21}$NO$_3$: C, 71.05; H, 7.37; N, 4.87. Found: C, 70.90; H, 7.38; N, 4.67.

EXAMPLE 10

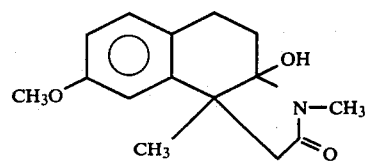
(Xb)

3,9b-Dimethyl-3a-hydroxy-8-methoxy-2-oxo-2,3,3a,4,5,9b-hexahydro-1H-benz[e]indole The solution of 22.0 g (79.7 mmol) ethyl-7-methoxy-1-methyl-2-oxo-1,2,3,4-tetrahydro-1-naphthaleneacetate (IXb) and 7.5 g (240 mmol) methylamine in 25 ml ethanol was left at room temperature for 24 hr. The crystalline precipitate formed was separated to give 15.5 g (74.5%) Xb, m.p. 182°–186°. From the mother liquor, after evaporation (35°) and treatment with ether, 1.0 g, additional Xb was collected increasing the yield to 79.5%; IR (Nujol), 3300 (OH), 1670 cm$^{-1}$ (lactam); NMR (CDCl$_3$-DMSO) δ, 1.48 (s, 3, CH$_3$), 2.82 (s, 3, N—CH$_3$), 3.78 (s, 3, OCH$_3$), 6.6–7.1 (m, 3, ArH).

Anal. Calcd. for C$_{15}$H$_{19}$NO$_3$: C, 68.94; H, 7.32; N, 5.36. Found: C, 68.74; H, 7.30; N, 5.53.

EXAMPLE 11

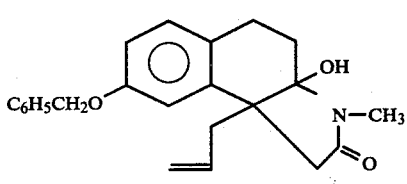
(Xc)

9b-Allyl-8-benzyloxy-3a-hydroxy-3-methyl-2-oxo-2,3,3a,4,5,9b-hexahydro-1H-benz[e]indole A mixture of 6.30 g (167 mmol) ethyl-1-allyl-7-benzyloxy-2-oxo-1,2,3,4-tetrahydro-1-naphthaleneacetate (IXc), 31.0 g methylamine and 200 ml 1:1 ethanol-dioxane was stirred at room temperature for 3 days. The reaction mixture was concentrated by evaporation of the solvent (35°–40° C.) to half the volume and diluted with 200 ml ether to provide a crystalline product which was collected to give 51.0 g (86%) Xc, m.p. 188°–190°; IR (Nujol), 3250, (broad), 1665, 1615, 1505 cm$^{-1}$.

Anal. Calcd. for C$_{23}$H$_{25}$NO$_3$: C, 76.00; H, 6.93; N, 3.85. Found: C, 75.89; H, 6.87; N, 3.90.

EXAMPLE 12

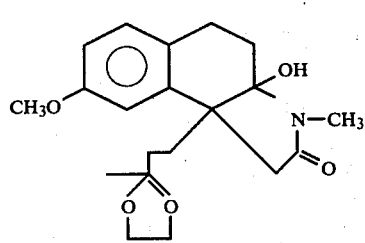
(Xd)

9b-(3-Ethylenedioxy)butyl-8-methoxy-3a-hydroxy-3-methyl-2-oxo-2,3,3a,4,5,9b-hexahydro-1H-benz[e]indole To a solution of 15.0 g (0.5 mole) methylamine in 50 ml ethanol was added 30.0 g (80 mmol) of ethyl-1-(3-ethylenedioxy)butyl-7-methoxy-2-oxo-1,2,3,4-tetrahydro-1-naphthaleneacetate (IXd). After standing at room temperature for 49 hr, the solvent was removed by evaporation to provide Xd as a dark-brown syrup which was used without further purification in Example 16.

EXAMPLE 13

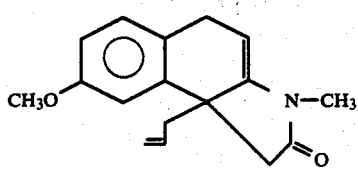

(XIa)

9b-Allyl-8-methoxy-3-methyl-2-oxo-2,3,5,9b-tetrahydro-1H-benz[e]indole

A solution of 14.0 g (48.7 mmol) Xa and 24 mg p-toluenesulfonic acid in 100 ml benzene was refluxed for 2 hr with azeotropic distillation of water using a Dean-Stark trap. After cooling to room temperature, the solution was washed with water and dried. Removal of the solvent on a rotary evaporator gave 13.0 g (100%) XIa as a pale-yellow syrup; IR (neat) 1725, 1685, 1615, 1505 cm$^{-1}$; NMR $\delta$2.24 (d, 2, allylic, J=7.0 Hz), 2.75 (s, 2, CH$_2$CO), 2.94 (s, 3, NCH$_3$), 3.34 (m, s, benzylic), 3.75 (s, 3, OCH$_3$), 4.75-5.85 (m, 4, olefinic), 6.5-7.2 (m, 3, ArH).

Anal. Calcd. for C$_{17}$H$_{19}$NO$_2$: C, 75.80; H, 7.11; N, 5.20. Found: C, 75.93; H, 7.10; N, 5.19.

EXAMPLE 14

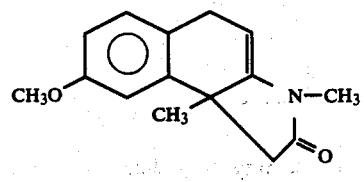

(XIb)

3,9b-Dimethyl-8-methoxy-2-oxo-2,3,5,9b-tetrahydro-1H-benz[e]indole

A solution of 11.25 g (43.2 mmol) and 25 mg p-toluenesulfonic acid in 100 ml toluene was refluxed for 2 hr with azeotropic removal of water. After cooling to room temperature, the solution was washed with water and dried (Na$_2$SO$_4$). Removal of the solvent in vacuo and trituration of the residue with ether (20 ml) gave 9.5 g (90%) crystalline XIb, m.p. 106°-108°; IR (CHCl$_3$) 1725, 1685 cm$^{-1}$; NMR $\delta$, 1.27 (s, 3, CH$_3$), 2.72 and 2.76 (s, 2, CH$_2$CO), 2.95 (s, 3, NCH$_3$), 3.34 (m, 2, benzylic), 3.78 (s, 3, OCH$_3$), 5.14 (dd, 1, NC=CH, J$_1$=5.0, J$_2$=3.5 Hz), 6.7-7.3 (m, 3, ArH).

Anal. Calcd. for C$_{15}$H$_{17}$NO$_2$: C, 74.04; H, 7.04; N, 5.75. Found: C, 74.28; H, 7.06; N, 5.89.

Crude XIb, obtained in quantitative yield as a solid, was used without purification in Example 18.

EXAMPLE 15

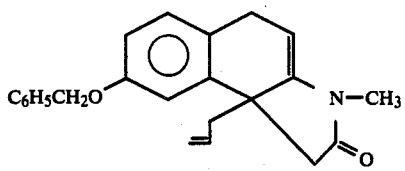

(XIc)

9b-Allyl-8-benzyloxy-3-methyl-2-oxo-2,3,5,9b-tetrahydro-1H-benz[e]indole

This compound was obtained quantitatively from Xc by the procedure of Example 14 and was used in Example 19 without further purification; IR (neat) 1725, 1685, 1610, 1505 cm$^{-1}$; NMR $\delta$, 2.26 (d, 2, allylic, J=7.0 Hz), 2.78 (s, 2, CH$_2$CO), 3.0 (s, 3, NCH$_3$), 3.41 (m, 2, benzylic), 4.8-5.8 (m, 6, olefinic, PhCH$_2$O), 6.7-7.6 (m, 8, ArH).

EXAMPLE 16

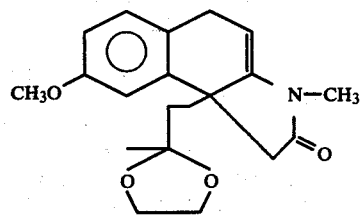

(XId)

9b-(3-Ethylenedioxy)butyl-8-methoxy-3-methyl-2-oxo-2,3,5,9b-tetrahydro-1H-benz[e]indole Crude Xd from Example 12 was dissolved in toluene, 50 mg p-toluenesulfonic acid added and the solution refluxed for 1 hr with azeotropic removal of water. The solvent was removed by evaporation and the residue was dissolved in ethanol (25 ml), diluted with ether (120 ml) and allowed to crystallize at room temperature. The crystalline XId was separated by filtration to give 7.0 g. The mother liquor, after evaporation to dryness, was dissolved with a small amount of CH$_2$Cl$_2$ and passed through a sintered glass funnel packed with silica (6 cm long×9.5 cm I.D.) and washed with 4% EtOH—CH$_2$Cl$_2$. After evaporation of the solvent, the dark-brown residue, 14.0 g, was dissolved in ether (50 ml) and allowed to crystallize at room temperature. The crystalline precipitate was filtered to give 5.0 g, additional XId. The mother liquor on cooling to 0° overnight deposited 1.0 g of XId. The above crystalline crops were combined to provide a total of 13.0 g (48%) XId. TLC on silica (4% EtOH—CH$_2$Cl$_2$) showed one major spot and a trace of another with lower Rf value. Recrystallization from ethanol (35 ml)-ether (20 ml) gave 10.0 g analytically pure XId, m.p. 143°-145°; IR (CHCl$_3$) 1725, 1680, 1610, 1505 cm$^{-1}$; NMR $\delta$, 1.18 (s, 3, CH$_3$), 2.80 (s, 2, CH$_2$CO), 3.0 (s, 3, NCH$_3$), 3.80 (s, 7, OCH$_2$CH$_2$O and OCH$_3$), 5.25 (dd, 1, NC=CH, J$_1$=3.5 and J$_2$=5.0 Hz), 6.70-7.35 (m, ArH).

Anal. Calcd. for C$_{20}$H$_{25}$NO$_4$: C, 69.94; H, 7.33; N, 4.07. Found: C, 69.45; H, 7.67; N, 4.29.

EXAMPLE 17

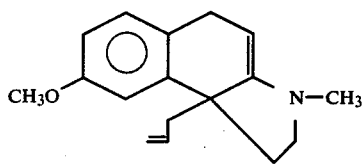
(IIa)

9b-Allyl-8-methoxy-3-methyl-5,9b-dihydrobenz[e]indoline

To a suspension of 5.9 g (155 mmol) lithium aluminum hydride in 190 ml dry ether was added dropwise under a slow stream of nitrogen and stirring a solution of 28.19 g (104.8 mmol) XIa in 190 ml dry ether at such a rate as to maintain gentle refluxing. Following the addition (20 min), stirring at room temperature was continued for 2 hrs. The reaction mixture was cooled in an ice bath and treated successively with 5.9 ml water, 4.4 ml 20% aqueous sodium hydroxide and 20.6 ml water to provide a granular precipitate which was filtered under nitrogen and rinsed with ether. The combined filtrate and washings were evaporated to dryness on a rotary evaporator under reduced pressure. After removal of the solvent was complete, the flask containing the product was filled with nitrogen. The compound IIa thus obtained consisted of a pale yellow syrup, 26.2 g (98%) and was used in Example 22 immediately after preparation; IR (neat) 1670 cm$^{-1}$ (N—C=C); NMR $\delta$, 2.60 (s, 3, N—CH$_3$), 3.68 (s, 3, OCH$_3$), 4.30 (dd, 1, NC=CH, J$_1$=5.5, J$_2$=2.5 Hz), 4.63–5.98 (m, 3, olefinic), 6.43–7.0 (m, 3, ArH).

IIa picrate. When very pure IIa was required and also for storing purposes, IIa was converted to the picrate salt as follows. IIa (26.2 g) was dissolved in 30 ml ethanol under nitrogen and the solution was added to a boiling solution of 30 g. picric acid in 200 ml ethanol. The crystalline precipitate was separated by filtration and dried to give 45.0 g (90%), m.p. 147°–148°.

Anal. Calcd. for C$_{23}$H$_{24}$N$_4$O$_8$: C, 57.02; H, 5.00; N, 11.56. Found: C, 57.15; H, 5.35; N, 11.61.

The picrate salt of IIa is a stable compound and could be stored at room temperature for several months. The enamine IIa was regenerated from its picrate as follows: A mixture of finely powdered picric acid salt of IIa (10 mmol), 50 ml 1N aqueous lithium hydroxide, 20 ml ethanol and 100 ml ether was shaken in a separatory funnel under nitrogen until all the solids had dissolved. The ether phase was separated and washed with water, dried (MgSO$_4$) and evaporated to dryness to quantitatively give the free base.

EXAMPLE 18

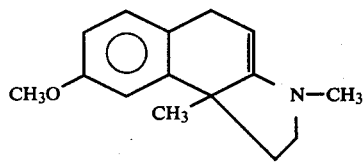
(IIb)

3,9b-Dimethyl-8-methoxy-5,9b-dihydrobenz[e]indoline

To a stirred suspension of 3.40 g (89.4 mmol) lithium aluminum hydride in 110 ml dry ether under a slow stream of nitrogen was added dropwise a solution of 14.65 g (60.2 mmol) of crude XIb in 500 ml dry ether and at such a rate as to maintain normal refluxing. After the addition (25 min), stirring was continued at room temperature for 1.5 hr. The product was isolated according to Example 17 to give 13.42 g (98%) of air sensitive XIb as a pale-brown liquid; IR (neat) 1675 cm$^{-1}$ (N—C=CH); NMR $\delta$, 1.20 (s, 3, CH$_3$), 2.67 (s, 3, N.CH$_3$), 3.74 (s, 3, OCH$_3$), 4.30 (dd, 1, NC=CH, J$_1$=5.5, J$_2$=2.5 Hz).

Anal. Calcd. for C$_{15}$H$_{19}$NO: C, 78.56; H, 8.35; N, 6.10. Found: C, 78.06; H, 8.24; N, 5.93.

When the reduction of XIb was carried out in ether-tetrahydrofuran, a sticky product was obtained which contained very little Ib as evidenced by NMR.

EXAMPLE 19

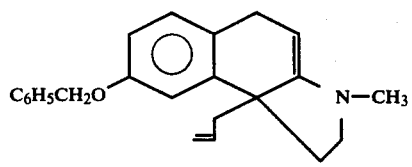
(IIc)

9b-Allyl-8-benzyloxy-3-methyl-5,9b-dihydrobenz[e]indoline

Reduction of crude XIc with lithium aluminum hydride in ether by the procedure of Example 17 afforded IIc; yield, 95% IR (neat) 1670 cm$^{-1}$., (NC=C); NMR $\delta$, 2.70 (s, 3, NCH$_3$), 4.36 (dd, 1, NC=CH, J$_1$=5.5, J$_2$=2.5 Hz), 4.73–5.90 (m, 3, olefinic), 5.08 (s, 2, PhCH$_2$O), 6.25–7.53 (m, 8, ArH).

EXAMPLE 20

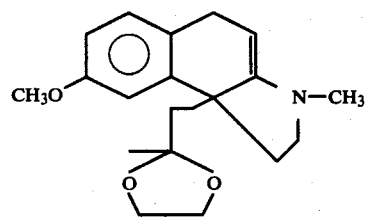
(IId)

9b-(3-Ethylenedioxy)butyl-8-methoxy-3-methyl-5,9b-dihydrobenz[e]indoline

To a suspension of 0.5 g (13 mmol) lithium aluminum hydride in 50 ml dry ether was added portionwise, under nitrogen and stirring 3.43 g (10 mmol) of crystalline XId. After the addition (15 min), the mixture was refluxed (maintaining the nitrogen atmosphere and stirring) for 45 min. Then, 30 ml ether was added and refluxing continued for a total of 2.5 hrs under nitrogen and stirring. The reaction mixture was cooled in an ice-bath and excess lithium aluminum hydride was decomposed by dropwise addition of water (0.6 ml). After stirring for 45 min, the hydrolyzed mixture was filtered under nitrogen and the filter-cake washed with ether. The ether solution after drying was evaporated to dryness to give 3.1 g (94%) of IId as a pale yellow syrup; IR (neat) 1670 cm$^{-1}$; NMR $\delta$, 1.20 (s, 3, CH$_3$), 2.65 (s, 3, NCH$_3$), 3.80 (s, 7, OCH$_2$CH$_2$O and OCH$_3$), 4.41 (dd, 1, NC=CH, J$_1$=5.5, J$_2$=2.5 Hz).

EXAMPLE 21

Bromination of benz[e]indolines of formula II

Method A. To a 0.1 M solution of bromine in methylene chloride previously cooled to −60° (acetone-dry ice) under nitrogen and stirring was added all at once an equimolar amount of a benz[e]indolines of formula II in the same solvent (1 mmol in 0.5–1.0 ml). After stirring in cold for 10–15 min and at room temperature for 20–30 min the solvent was removed in vacuo.

Method B. To a 0.1M solution of a benz[e]indoline of formula II in methylene chloride previously cooled to −60°, under nitrogen and stirring was added dropwise (20 min) an equimolar amount of bromine in the same solvent (1 mmol in 1.0–2.0 ml). After stirring in cold for 10–15 min and at room temperature for 20–30 min the solvent was removed in vacuo.

EXAMPLE 22

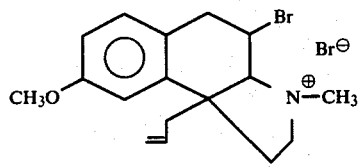

9b-Allyl-4-bromo-8-methoxy-2,4,5,9b-tetrahydro-1H-benz[e]indole methobromide Bromination of IIa according to Example 21 (method A) gave a quantitative yield of IIIa as a light-brown sticky product. This product without purification was used soon after preparation in Example 26.

When IIa was brominated according to Example 21 (method B), the bromination product contained an appreciable amount of the hydrobromide of IIa.

EXAMPLE 23

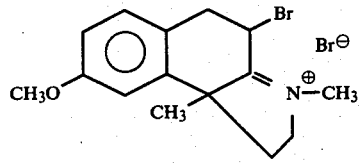

4-Bromo-9b-methyl-8-methoxy-2,4,5,9b-tetrahydro-1H-benz[e]indole methobromide Compound IIb, 13.4 g (58.6 mmol) was brominated according to Example 21 (method A). After removal of the solvent by evaporation, the sticky residue on trituration with ether solidified. Removal of the ether by evaporation gave 22.8 g (100%) crystalline. IIIb of pale yellow color. An analytical sample was prepared by recrystallization from ethanol, m.p. 125°–127°.

Anal. Calcd. for $C_{15}H_{19}Br_2NO \cdot \frac{1}{2}H_2O$: C, 45.24; H, 5.06; Br, 40.13; N, 3.54. Found: C, 45.37; H, 5.10; Br, 39.15; N, 3.51.

EXAMPLE 24

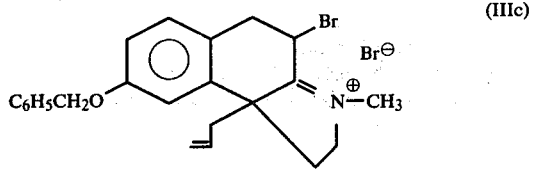

9b-Allyl-8-benzyloxy-4-bromo-2,4,5,9b-tetrahydro-1H-benz[e]indole methobromide The benz[e]indoline IIc, 51.2 g (154 mmol) was brominated according to Example 21 (method A) to yield 75.5 g (100%) crude IIIc as a sticky residue which was used in Example 29 without further purification.

EXAMPLE 25

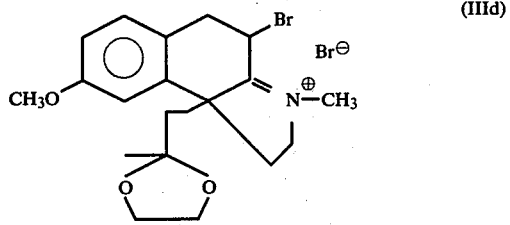

9b-(3-Methylenedioxy)butyl-4-bromo-8-methoxy-2,4,5,9b-tetrahydro-1H-benz[e]indole methobromide This compound was prepared in quantitative yield (crude) from IId according to Example 21 (method A) and utilized in Example 30 without further purification.

EXAMPLE 26

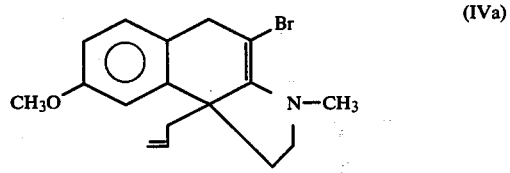

9b-Allyl-4-bromo-8-methoxy-3-methyl-5,9b-dihydrobenz[e]indoline (a) To a cold solution (−10°) of 3.75 g (9.05 mmol) IIIa in 55 ml 95% ethanol-water under nitrogen and stirring was added dropwise (45 min) 20 ml of 0.5M solution of ammonium bicarbonate in water. After stirring for 30 min more at the above temperature, the crystalline precipitate was fast filtered under nitrogen and dried in a flask under high vacuum. The flask was then filled with nitrogen. The pale yellow crystalline IVa (1.40 g, 47%) melted at 50°–60° (dec), IR (CHCl$_3$) 1670 cm$^{-1}$ (strong, N—C≡C); NMR δ, 1.85–2.35 (m, 4, allylic and CH$_2$), 3.14 (s, 3, NCH$_3$), 3.76 (s, 3, OCH$_3$), 3.14–3.76 (m, 4, benzylic and NCH$_2$), 4.70–5.80 (m, 3, olefinic), 6.50–7.15 (m, 3, ArH).

(b) In another experiment, an aqueous solution of IIIa was treated with excess sodium bicarbonate and extracted with ether. The ether extract after evaporation gave IVa in 55% yield. The dark brown aqueous phase upon extraction with chloroform and removal of the solvent gave a dark brown sticky residue, presumably Va (R$_1$=R$_3$=methyl, R$_2$=allyl). The ethereal extract IVa when stirred overnight in 80% ethanol-water produced the 9-oxo-benzomorphan. Ia. Similar treatment of the chloroform extract did not produce any Ia.

(c) In another experiment, an aqueous solution of IIIa was treated with excess sodium hydroxide and extracted with ether. Evaporation of the ether solution left a syrup IVa in 10-15% yield. The major product was the chloroform soluble compound Va of Example 26(b). The product of the ether extract but not the chloroform extract could be converted to Ia by treatment with aqueous ethanol.

(d) In another experiment, IIIa was treated with excess ammonium hydroxide and extracted with ether. Evaporation of the ether left IV as a syrup in 15% yield.

EXAMPLE 27

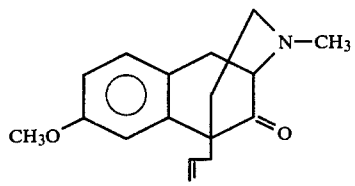

(Ia)

5-Allyl-2'-methoxy-2-methyl-9-oxo-6,7-benzomorphan.

Method A. Into a 250 ml 3-neck flask fitted with mechanical stirrer, dropping funnel and nitrogen inlet and outlet tubes was added a solution of 8.05 g (19.4 mmol) IIIa in 170 ml, 95% ethanol-water and the solution was cooled in an ice-bath and stirred under a slow stream of nitrogen. A solution of 1.58 g (20 mmol) ammonium bicarbonate in 42 ml water added dropwise in 1.5 hrs provided a pale yellow crystalline precipitate of IVa. After stirring in cold for 2 hr, the cooling bath was removed and the reaction mixture was stirred at room temperature for 24 hr. The dark brown solution was concentrated by evaporation to a volume of about 50 ml. alkalified with 10% sodium hydroxide (50 ml) and extracted with ether (3×50 ml) to a pale yellow solution.

After drying and removal of the solvent by evaporation, a syrup residue, 4.2 g, was left which was dissolved with 20 ml dry acetone and treated with a solution of 2.0 g anhydrous oxalic acid in 20 ml ether and allowed to crystallize first at room temperature and then at 0° overnight. The crystalline product obtained was separated by filtration to give 4.12 g (58.5%) of oxalate of Ia, m.p. 156°-159°. A sample was recrystallized from 94% ethanol-water to give the oxalate monohydrate that melted at 115°-120° solidified and melted at 160°-161°.

Anal. Calcd. for $C_{19}H_{23}NO_6 \cdot H_2O$: C, 60.15; H, 6.64; N, 3.69. Found: C, 60.09; H, 6.68; N, 3.56.

The yield of Ia was 64% when the crude product was purified by chromatography on activated aluminum oxide eluted with methylene chloride. The free base was obtained from the oxalate by base treatment and extraction with ether; IR (neat) 1730 cm$^{-1}$; NMR δ, 2.42 (s, 3, NCH$_3$), 3.75 (s, 3, OCH$_3$), 4.70-6.15 (m, 3, olefinic), 6.60-7.15 (m, 3, ArH).

In other runs, the ammonium bicarbonate or sodium bicarbonate was added all at once at the beginning of the reaction. The yields of Ia in these cases were 35-40%.

In another run, sodium hydroxide was used instead of ammonium bicarbonate. A product in 10-15% yield was obtained (of deep red color) which contained only traces of Ia as it was evidenced by the small absorption IR band at 1730 cm$^{-1}$. When ammonium hydroxide was used, the result was the same.

Method B. A mixture of 3.78 g (9.08 mmol) IIIa and 20.0 g aluminum oxide G type E for thin layer chromatography (Merck, Germany) in 40 ml 75% dimethylsulfoxide-water was stirred under nitrogen at room temperature for 24 hr. It was filtered and the cake washed with ethanol (2×15 ml) and water (2×20 ml). The combined filtrate and washings were diluted with water (50 ml), treated with 10% sodium bicarbonate (50 ml) and extracted with ether (4×50 ml). The ethereal extract was washed with water (3×50 ml) dried (MgSO$_4$), decolorized with Alumina Act. II (5.0 g) and filtered. Removal of the solvent by evaporation and treatment of the residue (1.7 g) with anhydrous oxalic acid as in Method A gave 1.80 g (55%) of the oxalate of Ia m.p. 156°-159°.

EXAMPLE 28

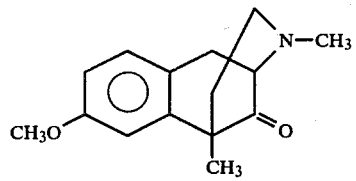

(Ib)

2'-Methoxy-2,5-dimethyl-9-oxo-6,7-benzomorphan (a) Exmploying the procedure of Example 27 (method A) a solution of 1.64 g (20.6 mmol) ammonium bicarbonate in 42 ml water was added dropwise in 1.5 hr under nitrogen to a solution of 7.78 g (20 mmol) crude IIIb in 175 ml, 95% ethanol-water, previously cooled in an ice-salt bath with stirring. After the addition, stirring in cold was continued for 2 hr and at room temperature for 24 hr. The brown solution was evaporated to near dryness and treated with 50 ml water and 50 ml 10% NaHCO$_3$ and extracted with ether (5×50 ml). The combined ethereal extracts were washed with water (2×50 ml) to a pale yellow solution. After drying (MgSO$_4$) and removal of the solvent by evaporation, the liquid residue (3.46 g, 70.6%) was dissolved with 10 ml dry acetone and treated with a solution of 2.0 g anhydrous oxalic acid in 10 ml acetone. The solution was allowed to crystallize first at room temperature and then at 0° overnight. The crystalline product was filtered and washed with acetone (20 ml) and dried to give 3.91 g (58%) of the oxalate of Ib, m.p. 136°-142°. The oxalate was quantitatively converted to the free base by treatment with ammonium hydroxide and extraction with chloroform. The free base shows a single spot on TLC (Alumina, 1% methanol in methylene chloride). The free base was dissolved in ether and converted to the hydrochloride (HCl, gas). Recrystallization of the hydrochloride from 95% ethanol-water gave the hydrochloride of the ethanol hemiacetal (no CO in IR; CH$_3$CH$_2$O— on NMR), m.p. 122°-144°. When the m.p. was taken slowly, the compound melted at 122° solidified and melted at 186°-188°. Recrystallization of the hydrochloride of Ib from water (2 ml/g)-acetone (10 ml/g) gave the hydrochloride monohydrate, m.p. 130°-132°.

The free base, IR (neat), 1730 cm$^{-1}$; NMR δ, 1.36 (s, 3, CH$_3$), 2.32 (s, 3, NCH$_3$), 3.65 (s, 3, OCH$_3$), 6.5-7.1 (m, 3, ArH).

(b) Employing the procedure of Example 27 (method B), a mixture of 3.89 g (10 mmol) IIIb and 23.0 g activated aluminum oxide in 90 ml, 75% DMSO-water was stirred under nitrogen for 24 hrs. It was filtered and the cake washed with ethanol (2×15 ml) and water (2×20 ml). The combined filtrate and washings was diluted with 250 ml water, treated with 10% NaHCO$_3$ (50 ml) and extracted with ether (7×50 ml). The ether extracts were washed with water (2×50 ml) dried and evaporated to dryness. The liquid residue (1.74 g, 71%) was converted to the oxalate as in Example 27 (method A) to give 1.97 g (58.5%) of Ib.

(c) Preparation according to the process of Takeda et al J. Org. Chem. 37, 2677 (1972). To a solution of 3.89 g (10 mmol) IIIb in 88 ml methylene chloride previously cooled in an ice-bath was added 25 ml water. After stirring for 30 min, aqueous ammonium hydroxide (30 ml of 3%) was added and stirring continued for 2 hr in cold and 20 hr at room temperature. The organic phase was separated and the aqueous phase extracted with chloroform (2×50 ml). The combined extracts (deep red color) were washed with water (2×50 ml), dried and evaporated to dryness to give 2.4 g dark red oil. TLC (Alumina, 1% MeOH—CH$_2$Cl$_2$) shows at least five spots. IR shows a band at 1730(CO) and a band at 1670 cm$^{-1}$ (NC=C) in a ratio of intensities of about 1:3 verifying the TLC observation that small amount of ketone was present in the mixture. The crude product was chromatographed on a column packed with Alumina Act. II to give a bed 19 cm long, 3.5 cm I.D. The column was eluted: (a) with 620 ml benzene to give 60 mg syrup; IR shows CO and NC=C. (b) after standing overnight it was eluted with 500 ml methylene chloride, removal of the solvent gave 50 mg syrup with same IR spectrum as the fraction above. (c) with 520 ml, 5% ethanol—CH$_2$Cl$_2$; removal of the solvent gave 1.1 g dark-red syrup; IR showed CO and N—C=C bands in a ratio of 2:1 (d) with methanol; removal of the solvent by evaporation gave 1.1 g dark-red sticky material. This was dissolved in methylene chloride washed with 10% NaHCO$_3$ (to convert any hydrobromide salt to the free base) dried and evaporated to dryness to give 0.9 g syrup, IR shows CO and NC=C bands.

The last two fractions (c and d) were combined and treated with ether (100 ml). Insoluble material was removed by filtration. The filtrate was washed with water (2×50 ml) to a pale yellow solution. After drying and removal of the solvent by evaporation, the liquid residue (0.9 g) was converted to the oxalate as above to give 0.7 g (21%) of Ib, m.p. 130°-138°.

EXAMPLE 29

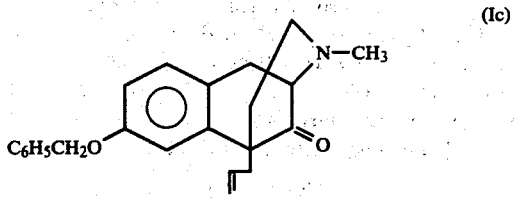

5-Allyl-2'-benzyloxy-2-methyl-9-oxo-6,7-benzomorphan

The compound IIIc (17.2 g, 35 mmol) was treated with ammonium bicarbonate in aqueous ethanol as described in Example 27 (method A) to give 10.7 g crude product as a syrup which was dissolved in dry-ether, polish filtered, and treated with an ethereal solution of anhydrous oxalic acid. The oxalate was recrystallized from 95% ethanol (10 ml)-acetone (40 ml) to give 7.4 g (42%) of the Ic oxalate, m.p. 104°-107°. IR (neat) of free base 1730 cm$^{-1}$; NMR δ, 2.40 (s, 3, NCH$_3$), 4.90 (s, 2, PhCH$_2$O), 4.85-6.15 (m, 3, olefinic), 6.60-7.30 (m, 8, ArH).

Anal. Calcd. for C$_{25}$H$_{27}$NO$_6$.H$_2$O: C, 65.91; H, 6.41; N, 3.07. Found: C, 65.17; H, 6.41; N, 2.89.

EXAMPLE 30

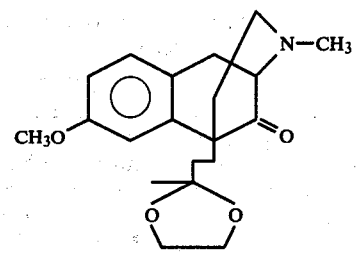

5-(3-Ethylenedioxy)butyl-2'-methoxy-3-methyl-9-oxo-6,7-benzomorphan

The crude bromoenaminium bromide IIId (9.1 mmol) was treated with ammonium bicarbonate in aqueous ethanol as described in Example 27 (method A). The crude product was purified by dry-column chromatography (silica, ether), to give 1.1 g (35.5%) Id as an oil. IR (neat) 1730 cm$^{-1}$; NMR δ, 1.40 (s, 3, CH$_3$), 2.47 (s, 3, NCH$_3$), 3.84 (s, 3, OCH$_3$), 3.98 (s, 4, OCH$_2$CH$_2$O), 6.7-7.2 (m, 3, ArH).

Anal. Calcd. for C$_{20}$H$_{27}$NO$_4$: C, 69.54; H, 7.88; N, 4.05. Found: C, 69.02; H, 7.63; N, 4.03.

EXAMPLE 31

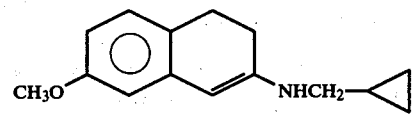

2-N-Cyclopropylmethylamino-7-methoxy-3,4-dihydronaphthalene

Into a 3-neck round-bottomed flask fitted with mechanical stirrer, a soxlet extractor packed with molecular sieves (50 g, type 3A), a condenser and a nitrogen inlet tube was added 10.75 g (100 mmol) cyclopropylmethylamine hydrochloride, 0.75 ml water (to solubilize the salt) and 10.1 g (100 mmol) triethylamine. After stirring for 10-15 min to liberate the cyclopropylmethylamine, a solution of 12.30 g (70 mmol) of 7-methoxy-2-tetralone in 100 ml benzene was used and the mixture (under nitrogen) was refluxed with stirring for 5 hrs. After cooling to room temperature, solids (triethylamine hydrochloride) were fast filtered off and washed on the funnel with ether (50 ml). The combined filtrate and washings were evaporated to dryness to give 15.8 g (99%) of XIIa as a pale yellow air-sensitive liquid; IR (neat), 3420 (NH), 1635 cm$^{-1}$ (C=C—N); NMR δ, 0.15-1.15 (m, 5, cyclopropyl), 2,15 (m, benzylic), 2.63-2.95 (m, 4, allylic and N—CH$_2$), 3.40 (broad, 1, NH), 3.75 (s, 3, OCH$_3$), 5.18 (s, 1, C-1H), 6.63-7.0 (m, 3, ArH).

Anal. Calcd. for $C_{15}H_{19}NO$: C, 78.57; H, 8.35; N, 6.11. Found: C, 78.93; H, 8.41; N, 6.03.

EXAMPLE 32

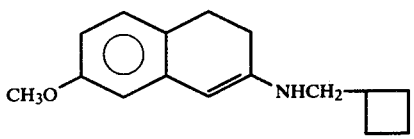
(XIIb)

2-N-Cyclobutylmethylamino-7-methoxy-3,4-dihydronaphthalene

Employing the procedure of Example 31, 7-methoxy-2-tetralone (70.4 g, 400 mmole) was reacted with cyclobutylmethylamine [generated in situ from 62.7 g (516 mmole) of its hydrochloride by treatment with an equimolar amount of triethylamine and 4.0 ml of water] in benzene (300 ml) to provide 93.40 g (96.5%) of XIIb as a pale yellow air-sensitive syrup; IR (neat), 3420 (NH), 1635 cm$^{-1}$ (C=C—N); NMR δ, 3.70 (s, 3, OCH$_3$), 5.15 (s, 1, C-1H), 6.25-6.90 (m, 3, ArH).

Anal. Calcd. for $C_{16}H_{21}NO$: C, 78.97; H, 8.69; N, 5.75. Found: C, 79.26; H, 8.73; N, 5.65.

EXAMPLE 33

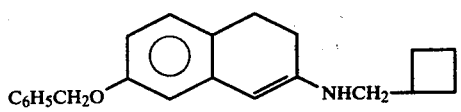
(XIIc)

7-Benzyloxy-2-N-cyclobutylmethylamino-3,4-dihydronaphthalene

Employing the procedure of Example 31, 7-benzyloxy-2-tetralone (3.65 g, 145 mmole) was reacted with cyclobutylmethylamine [generated in situ from 22.7 g (187 mmol) of its hydrochloride by treatment with an equimolar amount of triethylamine and 1.5 ml water] in benzene (110 ml) and the product isolated to yield 46.28 g (99%) of XIIc as a pale yellow, air-sensitive syrup; IR (neat), 3420 (NH), 1635 cm$^{-1}$ (C=C—N); NMR δ, 4.98 (s, 2, ArCH$_2$O), 5.15 (s, 1, C-1H), 6.35-7.40 (m, 8, ArH).

Anal. Calcd. for $C_{22}H_{25}NO$: C, 82.83; H, 7.89; N, 4.38. Found: C, 82.87; H, 7.79; N, 4.23.

EXAMPLE 34

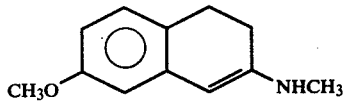
(XIId)

2-Methylamino-7-methoxy-3,4-dihydronaphthalene

This compound was prepared according to the procedure described by Evans, et al., J. Org. Chem. 35, 4122 (1970) as follows. Into a dry, nitrogen purged, 500 ml, 3-neck flask fitted with mechanical stirrer, dropping funnel and nitrogen inlet tube was added a solution of 14.3 g (460 mmole) methylamine in anhydrous ether (100 ml) and a solution of 20.0 g (113.5 mmole) 7-methoxy-2-tetralone in same solvent (100 ml) and the solution was placed under a slow stream of nitrogen and cooled to −18° (ice-methanol). A solution of 11.56 g (61 mmole) titanium tetrachloride in pentane (50 ml) was added dropwise with stirring over 30 min period. After the addition, the reaction mixture was stirred at room temperature for 1 hr and then fast filtered. The solid residue was washed with ether (50 ml) and the filtrate and washings were combined. Removal of the solvent in vacuo gave 20.6 g (96%) of XIId as an oxygen-sensitive oil which crystallized on standing; IR (neat), 3430 (NH), 1630 cm$^{-1}$ (C=C—N); NMR δ, 2.15 (m, 2, benzylic), 2.55 (m, 2, allylic), 2.70 (s, 3, NCH$_3$), 3.15 (broad, NH), 3.70 (s, 3, OCH$_3$), 5.13 (s, 1, C-1H), 6.25-6.90 (m, 3, ArH).

Anal. Calcd. for $C_{12}H_{15}NO$: C, 76.15; H, 7.99; N, 7.40. Found: C, 75.44; H, 7.92; N, 7.19.

EXAMPLE 35

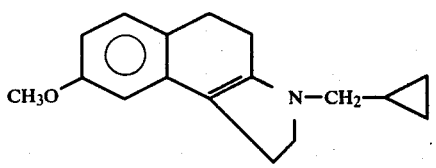
(XIIIa)

3-Cyclopropylmethyl-8-methoxy-1,2,4,5-tetrahydro-3H-benz[e]indole

This compound was prepared according to the procedure described by Evans, et al., J. Org. Chem. 35, 4122 (1970) for the synthesis of 3-methyl-1,2,4,5-tetrahydro-3H-benz[e]indole as follows. Into a dry, nitrogen filled, one liter 3-neck flask fitted with reflux condenser, serum cap, dropping funnel and magnetic stirrer, was added a solution of 38.55 g (167.9 mmol) XIIa in dry tetrahydrofuran (THF) (50 ml) which was placed under a slow stream of nitrogen. A 2.20 M solution of isopropyl magnesium chloride in THF (96.1 ml, 211.7 mmol) was added slowly via a syringe at such a rate as to maintain gently reflux. After the addition (15 min), 30.72 g (214.2 mmol) of bromochloroethan was added to the warm reaction mixture at a rate sufficient to maintain gentle refluxing. After the addition of the alkylhalide, an additional 52.3 ml (115 mmol) of the Grignard reagent was added to the reaction again at a controlled rate. The reaction mixture was cooled in an ice-bath and 270 ml of 1 M aqueous solution of ethylenediaminetetraacetic acid tetrasodium salt was added slowly (with stirring) and then 600 ml of a 1:1 etherbenzene was added. The organic layer was separated and the aqueous phase was extracted with ether. The combined extracts were washed with water (2×100 ml) and dried (MgSO$_4$). Removal of the solvent by evaporation gave 43.0 g (99%) of XIIIa as a pale yellow oxygen-sensitive oil; IR (neat), 1635 cm$^{-1}$ (C=C—N).

Anal. Calcd. for $C_{17}H_{21}NO$: C, 79.96; H, 8.29; N, 5.48. Found: C, 79.86; H, 8.35; N, 5.41.

EXAMPLE 36

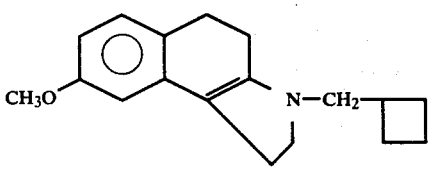
(XIIIb)

3-Cyclobutylmethyl-8-methoxy-1,2,4,5-tetrahydro-1H-benz[e]indole

Employing the procedure of Example 35, compound XIIb (93.4 g) was converted to XIIIb (98.0 g, 94.5%); pale brown oxygen-sensitive oil; IR (neat), 1635 cm$^{-1}$ (C=C—N).

Anal. Calcd. for $C_{18}H_{23}NO$: C, 80.25; H, 8.60; N, 5.19. Found: C, 80.15; H, 8.71; N, 5.09.

EXAMPLE 37

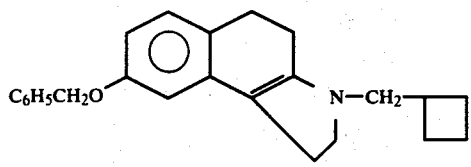
(XIIIc)

8-Benzyloxy-3-cyclobutylmethyl-1,2,4,5-tetrahydro-1H-benz[e]indole

Employing the procedure of Example 35, compound XIIc (46.0 g) was converted to XIIIc; yield 48.0 g (98%); IR (CHCl$_3$), 1635 cm$^{-1}$ (C=C—N).

Anal. Calcd. for $C_{24}H_{26}NO$: C, 83.43; H, 7.87; N, 4.06. Found: C, 83.72; H, 7.77; N, 3.96.

EXAMPLE 38

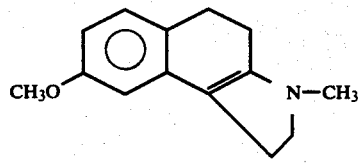
(XIIId)

3-Methyl-8-methoxy-1,2,4,5-tetrahydro-1H-benz[e]indole

Employing the procedure of Example 35, compound XIId (19.0 g) was converted to XIIId, yield 20.6 g (96%); IR (neat), 1635 cm$^{-1}$ (C=C—N); NMR, 2.62 (s, 3, NCH$_3$), 3.75 (s, 3, OCH$_3$), 6.6–7.1 (m, 3, ArH). This material was used in Example 42.

A sample was converted to the picrate salt; m.p. 108.5°–110°. (acetone-ether).

Anal. Calcd. for $C_{20}H_{21}N_4O_8$: C, 53.93; H, 4.75; N, 12.58. Found: C, 53.79; H, 4.65; N, 12.68.

EXAMPLE 39

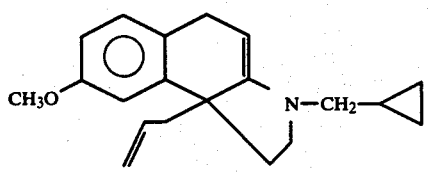
(IIe)

9b-Allyl-3-cyclopropylmethyl-8-methoxy-5,9b-dihydrobenz[e]indoline (a) Preparation From 3-cyclopropylmethyl-8-methoxy-1,2,4,5-tetrahydro-3H-benz[e]indole XIIIa. A solution of 43.0 g (167.9 mmol) XIIIa and 25.0 g (206 mmol) of allyl bromide in dry benzene (120 ml) was refluxed with stirring under a nitrogen atmosphere for 10 hrs. An oily precipitate was formed. After cooling to room temperature, the supernatant liquor was decanted and the residue was treated with acetone (50 ml) to provide a crystalline precipitate which was filtered to give 36.3 g (57.5%) of XIVa ($R_1$=methyl, $R_2$=allyl, $R_3$=cyclopropylmethyl, X=Br), m.p. 160°–165°. An analytical sample was obtained by crystallization from acetone-ether, m.p. 172°–174°.

Anal. Calcd. for $C_{20}H_{26}BrNO$: C, 63.84; H, 6.94; Br, 21.24. Found: C, 63.94; H, 6.94; Br, 21.13.

The yield of crystalline XIVa was 67% when acetonitrile was used as the solvent in place of benzene in the above procedure.

Benz[e]indoline IIe was quantitatively obtained from the hydrobromide XIVa by treatment with 10% aqueous sodium hydroxide and extraction with ether. IR (neat), 1670 cm$^{-1}$ (C=C—N); NMR δ, 3.77 (s, 3, OCH$_3$), 4.35 (broad, 1, NC=CH), 4.75–5.91 (m, 3, olefinic), 6.5–7.1 (m, 3, ArH).

(b) Preparation From 1-allyl-1-[2-(N-cyclopropylmethylamino)ethyl]-2,2-ethylenedioxy-7-methoxy-1,2,3,4-tetrahydronaphthalene (XIXa). To a solution of 30.4 g (85 mmole) XIXa in ethanol (125 ml) was added a solution of 4% hydrochloric acid (125 ml). The reaction mixture was stirred at room temperature overnight (16 hrs) and then concentrated under vacuum to about half volume, alkalified with 10% sodium hydroxide and extracted with ether (2×100 ml). Combined extracts were washed with water (2×80 ml) and dried (MgSO$_4$). Removal of the solvent under vacuum gave 23.0 g (92%) IIe identical with the material prepared in Example 39(a) above.

EXAMPLE 40

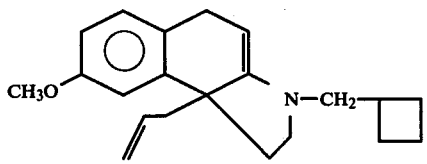
(IIf)

9b-Allyl-3-cyclobutylmethyl-8-methoxy-5,9b-dihydrobenz[e]indoline (a) Preparation From 3-cyclobutylmethyl-8-methoxy-1,2,4,5-tetrahydro-1H-benz[e]indole (XIIIb). A solution of 18.0 g (67 mmol) XIIIb and 10.5 g (87 mmol) allyl bromide in dry acetonitrile (60 ml) was refluxed under a nitrogen atmosphere for 16 hrs. After removal of the solvent in vacuo, the residue was treated with acetone (50 ml) and the crystalline product collected to give 15.5 g (59%) of XIVb ($R_1$=methyl, $R_2$=allyl, $R_3$=cyclobutylmethyl, X=Br), m.p. 168°–170°.

Anal. Calcd. for $C_{21}H_{28}BrNO$: C, 64.61; H, 7.23; Br, 20.47. Found: C, 64.38; H, 7.25; Br, 20.35.

The yield of crystalline XIVb was 49% when benzene was used as the solvent in place of acetonitrile in the above procedure.

The benz[e]indoline IIf was quantitatively obtained from the hydrobromide XIVb by treatment with sodium hydroxide and extraction with ether; IR (neat), 1670 cm$^{-1}$ (C=C—N); NMR δ, 3.75 (s, 3, OCH$_3$), 4.36 (broad, 1, NC=CH), 4.75–5.9 (m, 3, olefinic), 6.5–7.1 (m, 3, ArH).

(b) Preparation From 1-allyl-1-[2-(N-cyclobutylmethylamino)ethyl]-2,2-ethylenedioxy-7-methoxy-1,2,3,4-tetrahydronaphthalene (XIXb). Compound XIXb (33.7

EXAMPLE 41

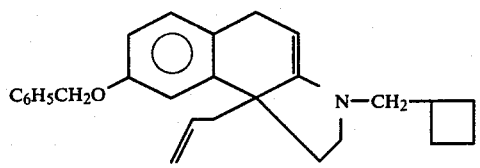

(IIg)

9-Allyl-8-benzyloxy-3-cyclobutylmethyl-5,9b-dihydrobenz[e]indoline

A mixture of 48.0 g (139 mmol) XIIIc and 21.9 g (181 mmol) allyl bromide in dry acetonitrile (140 ml) was refluxed under a nitrogen atmosphere for 16 hrs. After removal of the solvent by evaporation, the residue was treated with acetone (150 ml) and crystalline material collected to give 40.0 g (63%) of XIVc ($R_1$=benzyl, $R_2$=allyl, $R_3$=cyclobutylmethyl, X=Br), m.p. 181.5°–183.5°. An analytical sample was obtained by recrystallization from ethanol; m.p. 183°–184°.

Anal. Calcd. for $C_{27}H_{32}BrNO$: C, 69.52; H, 6.91; N, 3.00; Br, 17.13. Found: C, 69.56; H, 6.92; N, 2.90; Br, 16.96.

The enamine IIg was quantitatively obtained from the hydrobromide (XIVc) by treating with sodium hydroxide and extraction with ether; IR (neat), 1760 cm$^{-1}$ (C=C—N): NMR δ, 4.40 (broad, 1, NC=CH), 5.07 (s, 2, ArCH$_2$O), 4.73–5.90 (m, 3, olefinic), 6.75–7.5 (m, 8, ArH).

EXAMPLE 42

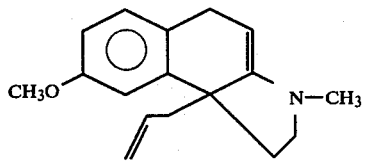

(IIa)

9b-Allyl-8-methoxy-3-methyl-5,9b-dihydrobenz[e]indoline

A solution of 5.04 g (23.4 mmol) XIIId and 3.70 g (30.5 mmol) allyl bromide in dry acetonitrile (20 ml) was refluxed for 16 hr under a nitrogen atmosphere. Removal of the solvent in vacuo left a sticky residue of XIVd ($R_1$=$R_3$=methyl, $R_2$=allyl, X=Br) which was purified by conversion to the picrate salt as follows. The hydrobromide XIVd (X=BR) was dissolved in water (100 ml) and extracted with ether (2×50 ml) to remove neutral material and these ethereal extracts were discharged. The aqueous phase was made alkaline with 10% sodium hydroxide (30%) and extracted with ether (2×70 ml). The ethereal solution was washed with water (3×30 ml), dried (MgSO$_4$) and the solvent removed in vacuo. The liquid residue (5.1 g) was dissolved in ethanol (20 ml) and added to a solution of 6.8 g picric acid in hot ethanol (50 ml) and allowed to crystallize at room temperature. The crystalline product was filtered to give 8.6 g (76%) of XIVd (X=picric acid), m.p. 143°–147°. An analytical sample obtained by crystallization from ethanol-acetone (1:15); m.p. 147°–148°, was identical with IIa prepared according to Example 17.

The yield of XIVd picrate was 66% when benzene was in place of acetonitrile in the above procedure.

The benz[e]indoline IIa regenerated from the picrate XIVd (X=picric acid) as follows: A mixture of finely powder picrate (10 mmol), 1 N aqueous lithium hydroxide (50 ml), ethanol (20 ml) and ether (100 ml) in a separatory funnel was shaken until all the picrate had dissolved. The ether phase was washed with water and, after drying, was evaporated to dryness to give the free base IIa quantitatively.

EXAMPLE 43

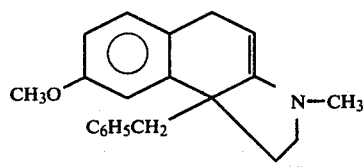

(IIh)

9b-Benzyl-8-methoxy-3-methyl-5,9b-dihydrobenz[e]indoline

A solution of 27.3 g (127 mmol) XIIId and 25.0 g (197 mmol) benzyl chloride in 130 ml dry acetonitrile was refluxed under a nitrogen atmosphere for 18 hrs. Removal of the solvent in vacuo left a residue XIVe ($R_1$=$R_3$=methyl, $R_2$=benzyl, X=Br) which resisted crystallization. The residue was dissolved in water (150 ml), extracted with ether (2×100 ml) to remove neutral material and the ethereal extracts were discharged. The aqueous phase was treated with 10% sodium bicarbonate (200 ml) and extracted with ether (3×100 ml). The combined ethereal extracts were washed with water (2×100 ml), dried, and the solvent removed in vacuo to give 30 g (78%) of IIh as a light brown syrup. The purity of this material was approximately 90% as estimated by NMR.

The crude benz[e]indoline IIh was treated with picric acid according to Example 42 to give 28.5 g. (42% based on XIIId) of the picric salt XIVe (X=picric acid) m.p. 123°–126° (crystallized from ethanol-acetone, 1:4).

Anal. Calcd. for $C_{27}H_{26}N_4O_8$: C, 60.66; H, 4.90; N, 10.48. Found: C, 59.99; H, 4.93; N, 10.52.

The benz[e]indoline IIh was quantitatively regenerated from the picrate by the procedure described in Example 42; IR (neat) 1670 cm$^{-1}$ (C=C—N); NMR δ, 2.65 (s, 3, NCH$_3$), 2.80 (s, 2, ArCH$_2$), 3.72 (s, 3, OCH$_3$), 4.37 (dd, 1, NC=CH, $J_1$=5.5, $J_2$=2.5 Hz), 6.50–7.35 (m, 8, ArH).

The yield of crude IIh was 60% when dioxane was used as the reaction solvent in place of acetontrile in the above procedure and the yield of the picrate ws 39%.

The yield of crude IIh was 10% where benzene was used as the reaction solvent in the above procedure.

EXAMPLE 44

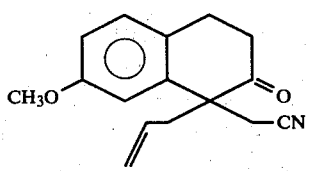

(XV)

1-Allyl-7-methoxy-2-oxo-1,2,3,4-tetrahydro-1-naph-
thaleneacetonitrile

1-Allyl-3,4-dihydro-7-methoxy-2(1H)-naphthalenone (VIIIa) 256.5 g (1.186 mole) in 250 ml dry dimethylformamide (DMF) was added dropwise to a stirred, cold (ice-bath) suspension of 24.86 g (1.186 mole) sodium hydride (or 49.92 g of 57% dispersion in oil washed with benzene) in 350 ml DMF under nitrogen. After the addition, (1 hr), the reaction mixture is stirred at room temperature for 2 hr and then cooled in an ice-bath. A solution of 89.54 g (1.186 mole) chloroacetonitrile in 300 ml dry DMF was added in a period of 1 hr, then the cooling bath removed and stirring continued at room temperature overnight. Water (1500 ml) and ether (300 ml) were added and on stirring a crystalline material precipitated. It was separated by filtration to give 210 g of XV. The organic phase in the filtrate was separated and the aqueous phase was extracted with benzene (4×200 ml). Combined extracts were washed with water (3×150 ml), dried and evaporated to dryness. The syrup residue was triturated with ether (200 ml) and on cooling it crystallized to give an additional 40.0 g product XV. The two crystalline crops were combined (250 g) and recrystallized from 1:1 ethanol-ether to give 231.0 g (76%) of compound XV, m.p. 90°–96°. A sample was distilled at 150°–160°/0.1 mm Hg and the distillate was crystallized from EtOH-ether to give an analytical sample, m.p. 94°–96°, IR (CHCl$_3$) 2250 (CN), 1715 cm$^{-1}$ (CO); NMR $\delta$, 3.77 (s, 3, OCH$_3$), 4.75–5.65 (m, 3, CH=CH$_2$), 6.65–7.15 (m, 3, ArH).

Anal. Calcd. for C$_{16}$H$_{17}$NO$_2$: C, 75.26; H, 6.71; N, 5.48. Found: C, 74.85; H, 6.97; N, 5.54.

EXAMPLE 45

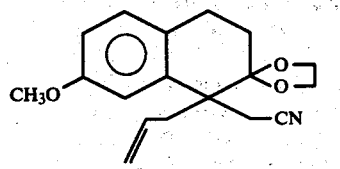

(XVI)

1-Allyl-2,2-ethylenedioxy-7-methoxy-1,2,3,4-tetrahydro-1-naphthaleneacetonitrile Into a round bottomed flask fitted with a Soxlet extractor packed with molecular sieves-3A (80 g), condenser and magnetic stirrer was added 71.5 g (0.2 mole) crude XV (m.p. 90°–96°), 90 ml ethylene glycol, 1.0 g p-toluenesulfonic acid and 250 ml dry toluene and the mixture was refluxed with stirring. At intervals (8–10 hrs), the sieves were replaced with fresh ones. After refluxing for 48 hrs the reaction mixture was cooled to room temperature and diluted with 10% NaHCO$_3$ (100 ml). The organic phase was separated and the aqueous phase extracted with benzene (2×50 ml). Combined extracts were washed with water and dried. Removal of the solvent by evaporation and trituration of the residue with ethanol (60 ml) gave 64.0 g (76%) of compound XVI, m.p. 82°–85°. A sample crystallized twice from the same solvent melted at 85°–86°; IR (CHCl$_3$), 2250, 1615, 1505; NMR $\delta$, 3.75 (s, 3, OCH$_3$), 4.06 (s, 4, OCH$_2$CH$_2$O), 4.85–6.0 (m, 3, olefinic), 6.6–7.15 (m, 3, ArH).

Anal. Calcd. for C$_{18}$H$_{21}$NO$_3$: C, 72.21; H 7.07; N, 4.68. Found: C, 72.23; H, 7.10; N, 4.50.

EXAMPLE 46

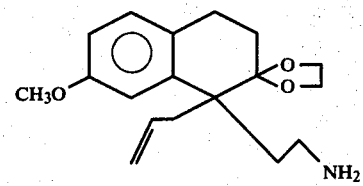

(XVII)

1-Allyl-2,2-ethylenedioxy-7-methoxy-1-(aminoethyl)-1,2,3,4-tetrahydronaphthalene A solution of 33.2 g (0.111 mole) of XVI in 480 ml dry ether was added dropwise under nitrogen and stirring to a suspension of 8.43 g (0.222 mole) lithium aluminum hydride in 210 ml dry ether. After the addition, (30 min), stirring at room temperature was continued for 48 hrs. The reaction mixture was cooled in an ice bath and excess hydride and the complex decomposed by dropwise addition, successively of 8.5 ml water, 6.4 ml 20% sodium hydroxide and 29.5 ml water. The granular inorganic precipitate thus obtained was filtered and rinshed with ether (100 ml) and the resulting ether solution dried (MgSO$_4$). Removal of the solvent in vacuo afforded 33.5 g (100%) of syrup XVII. The IR spectrum of the reduction production and TLC (alumina, CH$_2$Cl$_2$) affirmed the absence of any unreduced nitrile. A sample was purified by chromatography on an aluminum oxide column eluted first with methylene chloride to remove the impurities and then with ethanol to extract the product; NMR $\delta$, 1.05 (s, 2, NH$_2$), 3.70 (s, 3, OCH$_3$), 3.91 (s, 4, OCH$_2$CH$_2$O), 4.73–6.0 (m, 3, olefinic), 6.5–7.0 (m, 3, ArH).

Anal. Calcd. for C$_{18}$H$_{25}$NO$_3$: C, 71.25; H, 8.30; N, 4.61. Found: C, 70.74; H, 8.35; N, 4.50.

EXAMPLE 47

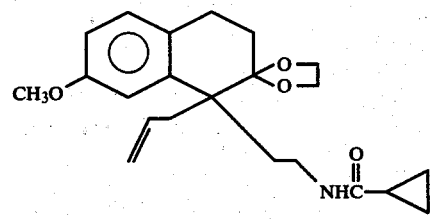

(XVIIIa)

1-Allyl-1-(2-cyclopropanecarboxamidoethyl)-2,2-ethylenedioxy-7-methoxy-1,2,3,4-tetrahydronaphthalene To an ice cold solution of 10.8 g (35.7 mmol) of crude XVII and 8.3 ml (60 mmole) triethylamine in 25 ml methylene chloride was added dropwise with stirring a solution of 4.18 g (40 mmol) cyclopropanecarbonyl chloride in 15 ml methylene chloride. After stirring for 1 hr in the cold and 2 hr at room temperature, it was washed with water and 10% sodium bicarbonate and dried (Na$_2$NO$_4$). Removal of the solvent by evaporation and trituration of residue with ether (50 ml) gave 10.5 g (79.5%) crystalline XVIIIa, m.p. 94°–95°, solidified and remelted at 114°–115°. The m.p. was unchanged when a sample recrystallized from 1:1 ethanol-ether; IR (CHCl$_3$), 3320 (NH), 1650 and 1555 cm$^{-1}$ (CO). NMR $\delta$, 0.3–0.8 (m, 5, cyclopropyl), 3.75 (s, 3, OCH$_3$), 4.0 (s, 4, OCH$_2$CH$_2$O), 4.75–6.0 (m, 3, olefinic), 6.50–7.10 (m, 3, ArH).

Anal. Calcd. for C$_{22}$H$_{29}$NO$_4$: C, 71.13; H, 7.87; N, 3.77. Found: C, 71.10, H, 8.03; N, 3.67.

EXAMPLE 48

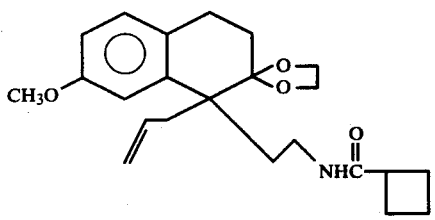
(XVIIIb)

1-Allyl-1-(2-cyclobutanecarboxamidoethyl)-2,2-ethylenedioxy-7-methoxy-1,2,3,4-tetrahydronaphthalene Reaction of XVII with cyclobutanecarbonyl chloride as described according to the procedure of Example 47 provided an 83% yield of XVIIIb, m.p. 99°–101° (crystallized from benzene-ligroin); NMR δ, 3.81 (s, 3, OCH$_3$), 4.06 (s, 4, OCH$_2$CH$_2$O), 4.86–6.05 (m, 3, olefinic), 6.6–7.1 (m, 3, ArH).

Anal. Calcd. for C$_{23}$H$_{31}$NO$_4$: C, 71.66; H, 8.10; N, 3.63. Found: C, 71.60; H, 8.21; N, 3.32.

EXAMPLE 49

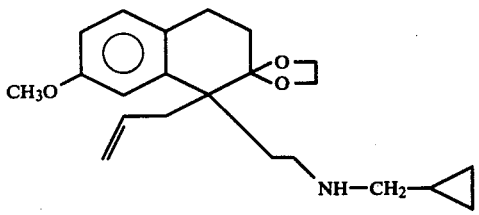
(XIXa)

1-Allyl-1-[2-(N-cyclopropylmethylamino)ethyl]-2,2-ethylenedioxy-7-methoxy-1,2,3,4-tetrahydronaphthalene To a suspension of 3.0 g (81 mmol) lithium aluminum hydride in dry ether (160 ml) was added dropwise with stirring a solution of 14.8 g (40 mmol) XVIIIa in dry THF (160 ml) at a rate to maintain gentle refluxing. After stirring at room temperature for 48 hrs, the reaction mixture was cooled in an ice-bath and the excess of hydride and the complex were decomposed by the successive dropwise addition of water (3.0 ml) 20% sodium hydroxide (2.25 ml) and water (10.5 ml). The inorganic precipitate was filtered and rinsed with ether (50 ml). The combined filtrate and washings, after drying (MgSO$_4$) were evaporated to dryness to give 14.0 g (98%) of XIXa as a syrup; NMR δ, 3.71 (s, 3, OCH$_3$), 3.95 (s, 4, OCH$_2$CH$_2$O), 4.7–6.0 (m, 3, olefinic), 6.5–7.0 (m, 3, ArH).

Anal. Calcd. for C$_{22}$H$_{31}$NO$_3$: C, 73.91; H, 8.74; N, 3.91. Found: C, 73.38; H, 8.89; N, 3.76.

EXAMPLE 50

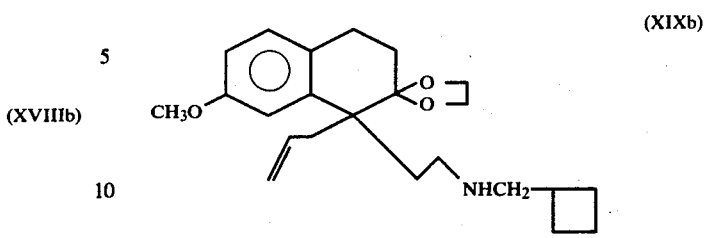
(XIXb)

1-Allyl-1-[2-(N-cyclobutylmethylamino)ethyl]-2,2-ethylenedioxy-7-methoxy-1,2,3,4-tetrahydronaphthalene Compound XIXb was obtained in 95% yield by reduction of XVIIIb according to the procedure of Example 49; NMR δ, 3.76 (s, 3, OCH$_3$), 4.0 (s, 4, OCH$_2$CH$_2$O), 4.8–6.0 (m, 3, olefinic), 6.60–7.10 (m, 3, ArH).

Anal. Calcd. for C$_{23}$H$_{33}$NO$_3$: C, 74.35; H, 8.95; N, 3.77. Found: C, 74.36; H, 9.13; N, 3.56.

EXAMPLE 51

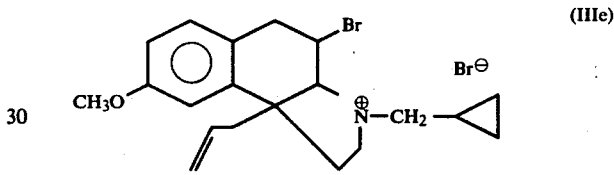
(IIIe)

9b-Allyl-4-bromo-8-methoxy-2,4,5,9b-tetrahydro-1H-benz[e]indole cyclopropylmethobromide To a solution of 11.9 g (74.5 mmol) bromine in 750 ml methylene chloride previously cooled in an acetone-dry ice bath under nitrogen and stirring was added all at once a solution of 22.06 g (74.5 mmol) of the enamine IIe in 50 ml methylene chloride. After stirring at the above temperature for 5 min and at room temperature for 20 min, the solvent was removed in vacuo leaving a solid residue which was triturated with ether (100 ml) and filtered to give 33.0 g (98.5%) of pale yellow color crystalline product IIIe, m.p. 112°–117°; IR (nujol) 1670 cm$^{-1}$.

Anal. Calcd. for C$_{20}$H$_{25}$Br$_2$NO: C, 52.76; H, 5.53; Br, 35.10. Found: C, 52.65; H, 5.48; Br, 34.96.

A sample recrystallized from ethanol melted at 133°–134°.

Anal. Found: C, 52.68; H, 5.79; Br, 35.05.

EXAMPLE 52

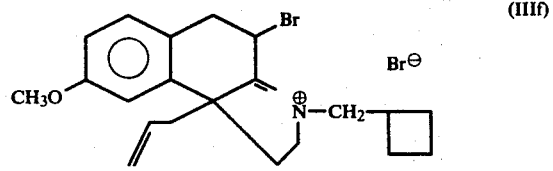
(IIIf)

9b-Allyl-4-bromo-8-methoxy-2,4,5,9b-tetrahydro-1H-benz[e]indole cyclobutylmethobromide The enamine IIf (10.0 g, 32.4 mmol) was brominated by the procedure of Example 51. After removal of the solvent in vacuo, the residue was dissolved in acetone (25 ml) and diluted with ether (50 ml). The pale yellow crystalline product was filtered to give 13.8 g (91%) of IIIf, m.p. 117°–120°.

Anal. Calcd. for $C_{21}H_{26}Br_2NO$: C, 53.86; H, 5.59; Br, 34.12; N, 2.99. Found: C, 53.88; H, 5.85; Br, 34.24; N, 2.86.

EXAMPLE 53

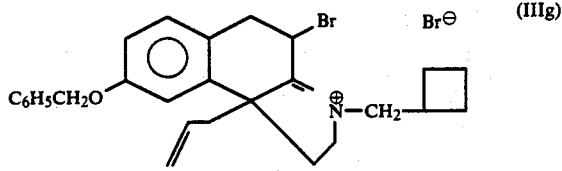

9b-Allyl-8-benzyloxy-4-bromo-2,4,5,9b-tetrahydro-1H-benz[e]indole cyclobutylmethobromide The enamine IIg (30.1 g, 78.2 mmol) was brominated by the procedure of Example 51. After removal of the solvent in vacuo, the solid residue was triturated with acetone (100 ml) and filtered to give 30.0 g (73%) of IIIg, m.p. 109°–112°. A sample crystallized twice from ethanol-ether melted at 114°–115°.

Anal. Calcd. for $C_{27}H_{31}Br_2NO$: C, 59.46; H, 5.72; Br, 29.30; N, 2.56. Found: C, 59.64; H, 5.88; Br, 29.12; N, 2.57.

EXAMPLE 54

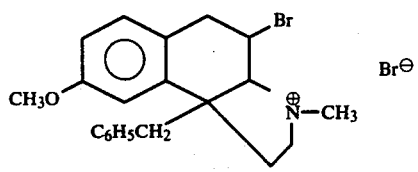

9b-Benzyl-4-bromo-8-methoxy-2,4,5,9b-tetrahydro-1H-benz[e]indole methobromide

The enamine IIh (14.0 g, 46.8 mmol) was brominated by the procedure of Example 51. Removal of the solvent in vacuo and trituration of the residue with acetone (50 ml) gave 17.2 g (82%) of pale yellow crystalline IIIh, m.p. 103°–106°.

Anal. Calcd. for $C_{21}H_{23}Br_2NO$: C, 54.21; H, 4.98; Br, 34.35. Found: C, 54.46; H, 5.01; Br, 34.08.

EXAMPLE 55

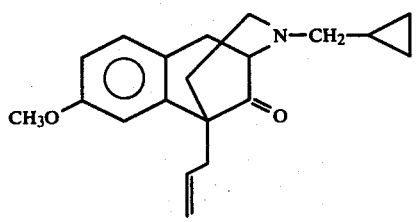

5-Allyl-2-cyclopropylmethyl-2'-methoxy-9-oxo-6,7-benzomorphan

Method A. From IIIe by treatment with ammonium bicarbonate. To a solution of 9.1 g (20 mmol) IIIe in 95% ethanol (170 ml), previously cooled in an ice-salt bath under nitrogen and stirring, was added dropwise in 1.5 hr period a solution of 1.70 g (21.5 mmol) ammonium bicarbonate in water (21 ml). Oily bromoenamine IVe ($R_1$=methyl, $R_2$=cyclopropylmethyl, $R_3$=allyl) had deposited on the sides of the flask. After the addition of the bicarbonate, the reaction mixture was stirred in cold for 2 hrs and at room temperature for 48 hrs. It was concentrated under reduced pressure to a small volume, the residue was treated with 10% sodium bicarbonate (50 ml) and extracted with ether (3×50 ml). The combined ethereal extracts were washed with water (3×30 ml), dried (MgSO4) and the solvent removed in vacuo to give 4.6 g of crude Ie. TLC on alumina with ether showed one major spot with Rf 0.78 (Ie) and a minor one with Rf 0. The syrup was dissolved in dry-acetone (10 ml), added to a solution of 2.0 g anhydrous oxalic acid in acetone (10 ml) and the resulting solution was diluted with dry-ether (10 ml). The crystalline product was filtered to give 4.0 g (50%) of the oxalate of Ie, m.p. 148.5°–150.0°.

Anal. Calcd. for $C_{22}H_{27}NO_6$: C, 65.82; H, 6.78; N, 3.48. Found: C, 65.57; H, 7.08; N, 3.40.

The free base Ie was regenerated quantitatively from the oxalate (sodium hydroxide-ether); IR (neat) 1730 $cm^{-1}$; NMR δ, 3.75 (s, 3, OCH3), 4.85–6.15 (m, 3, olefinic).

Method B. From IIIe by treatment with aluminum oxide. A mixture of 5.0 g (11 mmol) of IIIe and 25 g aluminum oxide G (type E for thin layer chromatography, Merck, Germany) in 50 ml of 75% dimethylsulfoxide-water was stirred under nitrogen for 24 hrs. The reaction mixture was filtered and the filter-cake washed with ethanol (2×25 ml) and water (2×20 ml). The filtrate and washings were combined, diluted with water (150 ml) and 10% sodium bicarbonate (50 ml) and extracted with ether (3×50 ml). After drying, the solvent was removed by evaporation and the liquid residue (2.70 g) was converted to the oxalate, to give 2.6 g (59%) of Ie oxalate, m.p. 148°–150°.

EXAMPLE 56

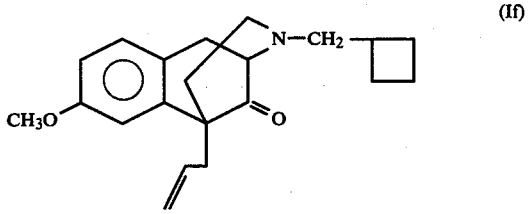

5-Allyl-2-cyclobutylmethyl-2'-methoxy-9-oxo-6,7-benzomorphan

The bromoenaminium bromide IIIf (46.9 g) was treated with ammonium bicarbonate by the procedure of Example 55. In the initial stages of the reaction, the bromoenamine IVf ($R_1$=methyl, $R_2$=allyl, $R_3$=cyclobutylmethyl) deposited on the sides of the flask and dissolved as the reactions progressed. The crude If was chromatographed on a column of aluminum oxide (22.5 cm long×6.5 cm I.D.) with methylene chloride and the portion containing If was evaporated to give 20.0 g (61.5%) syrup. The syrup, dissolved in dry acetone (60 ml), was added to a solution of 10.0 g anhydrous oxalic acid in dry acetone (50 ml) and diluted with dry ether (50 ml) to give 20.0 g (48%) of the oxalate of If, m.p. 176°–179°. The oxalate (slightly colored) was stirred with boiling acetone (100 ml) and after cooling, filtered to give 19.5 g, m.p. 182°–182.5°.

Anal. Calcd. for $C_{23}H_{29}NO_6$: C, 66.48; H, 7.03; N, 3.37. Found: C, 66.72; H, 6.99; N, 3.30.

The free base If was regenerated from the oxalate by treatment with sodium hydroxide and extraction with ether; IR (neat) 1730 cm$^{-1}$; NMR δ, 3.75 (s, 3, OCH$_3$), 4.85–6.15 (m, 3, olefinic).

EXAMPLE 57

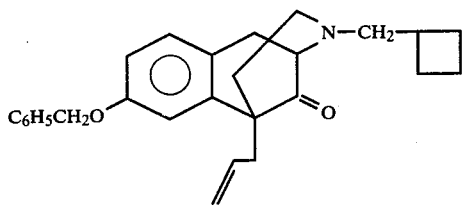

5-Allyl-2'-benzyloxy-2-cyclobutylmethyl-9-oxo-6,7-benzomorphan

A mixture of 5.45 g (10 mmol) IIIg and 25.0 g aluminum oxide in 75% dimethylsulfoxide-water (113 ml) was stirred at room temperature under nitrogen for 72 hrs. The reaction mixture was filtered and the filter-cake was washed with ethanol (2×15 ml) and water (2×20 ml). The combined filtrate and washings were diluted with water (250 ml) and 10% sodium bicarbonate (50 ml) and extracted with ether (5×60 ml). The ethereal extract was washed with water (3×60 ml), dried (MgSO$_4$) and decolorized with alumina (5.0 g). Removal of the solvent in vacuo left 3.0 g syrup Ig. The syrup was dissolved in dry acetone (10 ml), mixed with a hot solution of 1.2 g anhydrous oxolic acid in dry acetone (20 ml) and diluted with dry ether (30 ml). The crystalline product was filtered to give 2.5 g (51%) of the oxalate of Ig, m.p. 165°–167°.

The free base Ig was regenerated from the oxalate by treatment with sodium hydroxide and extraction with ether; IR (neat) 1730 cm$^{-1}$; NMR δ, 5.05 (s, 2, ArC-H$_2$O), 5.85–6.15 (m, 3, olefinic), 6.85–7.50 (m, 8, ArH).

The hydrobromide of Ig had m.p. 198°–199° (ethanol-ether).

Anal. Calcd. for $C_{27}H_{31}NO_2HBr$: C, 67.21; H, 6.68; N, 2.90. Found: C, 67.07; H, 6.83; N, 3.01.

EXAMPLE 58

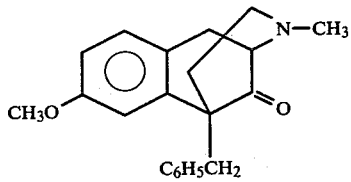

5-Benzyl-2'-methoxy-2-methyl-9-oxo-6,7-benzomorphan

Method A. From IIIh by treatment with ammonium bicarbonate. Following the procedure of Example 55 (Method A), 6.97 g (15 mmol) of IIIh in 150 ml 95% ethanol was treated with 1 M solution of ammonium bicarbonate (16.2 ml) and the reaction mixture stirred at room temperature for 72 hrs. In the initial stages of the reaction, the bromoenamine precipitaed out of the solution as a yellow crystalline product and slowly dissolved as the reaction progressed. The compound Ih was isolated and purified via the oxalate (21% yield), m.p. 150°–160°.

Method B. From IIIh by treatment with aluminum oxide. A mixture of 4.65 g (10 mmol) IIIh and 23 g activated aluminum oxide in 85% dimethylsulfoxide-water (90 ml) was stirred under nitrogen for 24 hrs. The product was isolated and purified by chromatography on Alumina Act. II with 1% ethanol-methylene chloride, to yield 0.51 g (15.4%) Ih, m.p. 136.5°–137.5° (ethanol); IR (CHCl$_3$) 1730 cm$^{-1}$; NMR δ, 2.40 (s, 3, NCH$_3$), 3.35 (s, 2, ArCH$_2$), 3.65 (s, 3, OCH$_3$), 6.6–7.2 (m, 3, ArH).

Anal. Calcd. for $C_{21}H_{23}NO_2$: C, 78.47; H, 7.21; N, 4.36. Found: C, 78.42; H, 7.28; N, 4.30

What is claimed is:

1. A compound having the formula

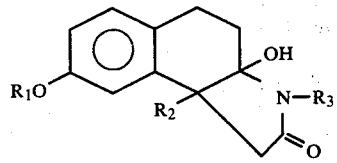

wherein
$R_1$ is lower alkyl or benzyl;
$R_2$ is selected from the group consisting of lower alkyl, allyl, benzyl and

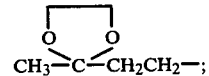

$R_3$ is selected from the group consisting of lower alkyl,

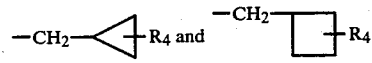

in which $R_4$ is hydrogen or methyl.

2. The compound of claim 1 wherein $R_1$ and $R_3$ are methyl and $R_2$ is allyl which is 9b-allyl-3a-hydroxy-8-methoxy-3-methyl-2-oxo-2,3,3a,4,5,9b-hexahydro-1H-benz[e]indole.

3. The compound of claim 1 wherein $R_1$, $R_2$ and $R_3$ are methyl which is 3,9b-dimethyl-3a-hydroxy-8-methoxy-2-oxo-2,3,3a,4,5,9b-hexahydro-1H-benz[e]indole.

4. The compound of claim 1 wherein $R_1$ is benzyl, $R_2$ is allyl, and $R_3$ is methyl which is 9b-allyl-8-benzyloxy-3a-hydroxy-3-methyl-2-oxo-2,3,3a,4,5,9b-hexahydro-1H-benz[e]indole.

5. The compound of claim 1 wherein $R_1$ and $R_3$ are methyl and $R_2$ is (3-ethylenedioxy)butyl which is 9b-(3-ethylenedioxy)butyl-8-methoxy-3a-hydroxy-3-methyl-2-oxo-2,3,3a,4,5,9b-hexahydro-1H-benz[e]indole.

* * * * *